United States Patent
Senkan

(10) Patent No.: US 6,426,226 B1
(45) Date of Patent: Jul. 30, 2002

(54) METHOD AND APPARATUS FOR SCREENING CATALYST LIBRARIES

(75) Inventor: Selim Mehmet Senkan, Los Angeles, CA (US)

(73) Assignee: Laboratory Catalyst Systems LLC, Los Angeles, CA (US)

( * ) Notice: Subject to any disclaimer, the term of this patent is extended or adjusted under 35 U.S.C. 154(b) by 0 days.

(21) Appl. No.: 09/697,162

(22) Filed: Oct. 27, 2000

Related U.S. Application Data

(63) Continuation of application No. PCT/GB99/03767, filed on Nov. 11, 1999, which is a continuation of application No. 09/191,849, filed on Nov. 12, 1998, now abandoned, which is a continuation-in-part of application No. 09/087,417, filed on May 29, 1998, now abandoned, which is a continuation-in-part of application No. 08/949,203, filed on Oct. 10, 1997, now abandoned.

(51) Int. Cl.[7] .......................... G01N 31/10; B01D 59/44; H01J 49/00

(52) U.S. Cl. ..................... 436/37; 250/281; 250/282; 250/283; 250/288; 436/147; 436/159; 436/172; 436/173; 422/83; 422/98

(58) Field of Search ................. 436/37, 147, 159, 436/164, 172–173; 250/281–283, 288; 422/83, 98

(56) References Cited

U.S. PATENT DOCUMENTS

| | | | |
|---|---|---|---|
| 4,026,958 A | | 5/1977 | Gryaznov et al. |
| 4,099,923 A | | 7/1978 | Milberger |
| 5,122,752 A | | 6/1992 | Koga et al. |
| 5,776,359 A | * | 7/1998 | Schultz et al. ............ 252/62.51 |
| 5,855,850 A | * | 1/1999 | Sittler .......................... 422/98 |
| 5,959,297 A | * | 9/1999 | Weinberg et al. ............ 250/288 |
| 6,063,633 A | * | 5/2000 | Willson, III .................. 436/37 |

FOREIGN PATENT DOCUMENTS

| | | |
|---|---|---|
| EP | 0 266 334 | 5/1988 |
| WO | WO 97/32208 | 9/1997 |
| WO | WO 98/15501 | 4/1998 |
| WO | WO 99/19724 | 4/1999 |

OTHER PUBLICATIONS

J. J. Hanak RCA Technical Report 1969, 11 pages.*
J. J. Hanak J. Mater. Sci. 1970, 5, 964–971.*
P. K. Schenck et al, J. Chem. Phys. 1981, 2547–2557.*
J. Boyle et al, Combust. Sci. Technol. 1990, 70, 187–203.*
S. P. Lee Int. J. Chem. Kinet. 1990, 22, 975–980.*
M. N. R. Ashfold Anal. Proc. (London) 1991, 28, 416–418.*
J. B. Simeonsson et al, Spectrochim. Acta 1994, 49B, 1545–1555.*
A.–P. Elg et al, Appl. Phys. B: Lasers Opt. 1997, 64, 573–578.*
H. Heinemann, "A Brief History of Industrial Catalysis", Catalysis Science and Technology, (Editors: J.R. Anderson et al.), Springer–Verlag, N.Y., vol. 1, pp. 1–11, (1981).

(List continued on next page.)

*Primary Examiner*—Arlen Soderquist
(74) *Attorney, Agent, or Firm*—Finnegan, Henderson, Farabow, Garrett and Dunner, L.L.C.

(57) ABSTRACT

Rapid screening for activities and selectivities of catalyst libraries having addressable test sites is achieved by contacting potential catalysts at the test sites with reactant streams forming product plumes at the adressable test sites. The product plumes are screened by translating a sample probe and/or the library to a position that one addressable site is in proximity to the sampling probe sample orifice and passing a portion of the reaction products through the sampling orifice forming a free jet expanded volume in at least one vacuum stage and passing a portion of the cooled and reduced pressure jet stream through an inlet orifice of a mass spectrometer for analysis. The mass spectrometric analysis may be combined with resonance enhanced multiphoton ionization methods of detection for very rapid library evaluation. Suitable reactors, microreactors, and product transfer sample microprobes for product transfer to a mass spectrometer are disclosed.

18 Claims, 26 Drawing Sheets

OTHER PUBLICATIONS

R. Baum, "Combinatorial Chemistry", Chemical & Engineering News, (2 pages), Feb. 12, 1996.

S. Borman, "Combinatorial Chemists Focus on Small Molecules, Molecular Recognition, and Automation", Chemical & Engineering News, (12 pages), Feb. 12, 1996.

A. Thayer, "Combinatorial Chemistry Becoming Core Technology at Drug Discovery Companies", Chemical & Engineering News, (8 pages), Feb. 12, 1996.

J. Krieger, "Combinatorial Chemistry Spawns New Software Systems to Manage Flood of Information", Chemical & Engineering News, (7 pages), Feb. 12, 1996.

J. Nielsen, "Combinatorial Chemistry", Chemistry & Industry, pp. 902–905, (1994).

X.–D. Xiang et al., "A Combinatorial Approach to Materials Discovery", Science, vol. 268, pp. 1738–1740, (1995).

G. Briceño et al., "A Class of Cobalt Oxide Magnetoresistance Materials Dsicovered with Combinatorial Synthesis", Science, vol. 270, pp. 273–275, (1995).

J. Wang et al., "Identification of a Blue Photoluminescent Composite Material from a Combinatorial Library", Science, vol. 279, pp. 1710–1713, (1998).

E. Danielson et al., "A combinatorial approach to the discovery and optimization of luminescent materials", Nature, vol. 389, pp. 944–948, (1997).

X. D. Sun et al., "Identification and optimization of advanced phosphors using combinatorial libraries", Appl. Phys. Lett., vol. 70, No. 25, pp. 3353–3355, (1997).

X. D. Sun et al., "Solution–Phase Synthesis of Luminescent Materials Libraries", Advanced Materials, vol. 9, No. 13, pp. 1046–1049, (1997).

M. Kassem et al., "Chemical Structure of Fuel–rich 1,2–$C_2H_4Cl_2/CH_4/O_2/$ Ar Flames: Effects of Micro–Probe Cooling on the Sampling of Flames of Chlorinated Hydrocarbons", Combust, Sci. and Tech., vol. 67, pp. 147–157, (1989).

F.C. Moates et al., "Infrared Thermographic Screening of Combinatorial Libraries of Heterogeneous Catalysts", Ind. Eng. Chem. Res., vol. 35, pp. 4801–4803, (1996).

T. Miyao et al., "CVD Synthesis of Alumina–supported Molybdenum Carbide Catalyst", Chemistry Letters, pp. 561–562, (1996).

M. B. Kizling, "A review of the use of plasma techniques in catalyst preparation and catalytic reactions", Applied Catalysis A: General 147, pp. 1–21, (1996).

Y.J. Kim et al., "Selective growth and characterization of pure, epitaxial $\alpha$–$Fe_2O_3$(0001) and $Fe_3O_4$(001) films by plasma–assisted molecular beam epitaxy", Surface Science 371, pp. 358–370, (1997).

A.A. Gorbunov et al., "Ultrathin film deposition by pulsed laser ablation using crossed beams", Applied Surface Science 96–98, pp. 649–655, (1996).

R.E. Russo et al., "Make catalytic coatings by pulsed–laser deposition", Chemtec, pp. 14–17, (1994).

C.N. Satterfield, "Heterogeneous catalysis in industrial practice", Second Edition, McGraw–Hill, Inc., pp. 87–130, (1991).

A.V. Lemmo et al., "Characterization of an inkjet chemical microdispenser for combinatorial library synthesis", Anal. Chem., vol. 69, pp. 543–551, (1997).

J.M. Smith, "Chemical engineering kinetics", Third Edition, McGraw–Hill Book Company, pp. 327–357, (1981).

K. Burgess et al., "New Catalysts and Conditions for a C — H Insertion Reaction Idendified by High Throughput Catalyst Screening", Angew. Chem. Int. Ed. Engl., vol. 35, pp. 220–222, (1996).

D. Lubman et al., "Resonant Two–Photon Ionization Spectroscopy of Biological Molecules in Supersonic Jets Volatilized by Pulsed Laser Desorption", Lasers and Mass Spectrometry, Oxford Univ. Press, N.Y., pp. 353–382, (1990).

R. Zimmerman et al., "Three–dimensional trace analysis: combination of gas chromatography, supersonic beam UV spectroscopy and time–of–flight mass spectrometry", Eur. Mass Spectrom., vol. 1, pp. 341–351, (1995).

C.M. Gittins et al., "Real–Time Quantitative Analysis of Combustion–Generated Polycyclic Aromatic Hydrocarbons by Resonance–Enhanced Multiphoton Ionization Time – of–Flight Mass Spectrometry", Anal. Chem., vol. 69, pp. 286–293, (1997).

M.J. Castaldi et al., "Real–Time, Ultrasensitive Monitoring of Air Toxics by Laser Photoionizaiton Time of Flight Mass Spectrometry", Journal of the Air and Waste Management Association, (8 pages), (1997).

D.H. Parker, "Laser Ionization Spectroscopy and Mass Spectrometry", Ultrasensitive Laser Spectroscopy, (Ed. D. Klieger), Academic Press, N.Y., pp. 233–309, (1983).

R. Tembreull et al., "Applicability of Resonant Two–Photon Ionization in Supersonic Bean Mass Spectrometry to Halogenated Aromatic Hydrocarbons", Analytical Chem., vol. 57, pp. 1186–1192, (1985).

K.C. Smyth et al., "Two–photon ionization processes of PO in a $C_2H_2$/air flame", J. Chem. Phys., vol. 77, pp. 1779–1787, (1982).

T.A. Cool, "Quantitative measurement of NO density by resonance three–photon ionization", Applied Optics, vol. 23, No. 10, pp. 1559–1572, (1984).

J.E.M. Goldsmith, "Resonant multiphoton optogalvanic detection of atomic oxygen in flames", J. Chem. Phys., vol. 78, No. 3, pp. 1610–1611, (1983).

G.C. Bjorklund et al., "Selective Excitation of Rydberg Levels in Atomatic Hydrogen by Three Photon Absorption", Optics Communications, vol. 31, No. 1, pp. 47–51, (1979).

D. M. Rebhan et al., "A Kinetic and Mechanistic Study of Cyclohexene Disproportionation: An Example of Irreversible Hydrogen Transfer", Journal of Catalysis, vol. 111, pp. 397–408, (1988).

R. Srinivasan et al., "Micromachined Reactors for Catalytic Partial Oxidation Reactions", AIChE Journal, vol. 43, No. 11, pp. 3059–3069, (1997).

Executive Summary "Catalysis Looks to the Future", Panel on New Directions in Catalytic Science and Technology Board on Chemical Sciences and Technology, National Research Council, National Academy Press, Washington, D.C.pp. 1–9, (1992).

R.F. Service, "High–Speed Materials Design", Science, vol. 277, pp. 474–475, (1997).

Ahmed et al., "Hydrogenation of cyclohexane and cyclohexene over supported nickel and platinum catalysts," Chemical Engineering Journal, 50, pp. 165–168 (1992).

D. Hensley, Chemicals and Catalysts:, Precious Metals Corporation, (2 page letter), (1997).

T.V. Venkitachalam et al., "Resonance–Enhanced Multiple- –Photon Ionisation Spectroscopy of Excited Sulphur Atoms", Appl. Phys. B. vol. 52, No. 2, pp. 102–107, (1991).

* cited by examiner

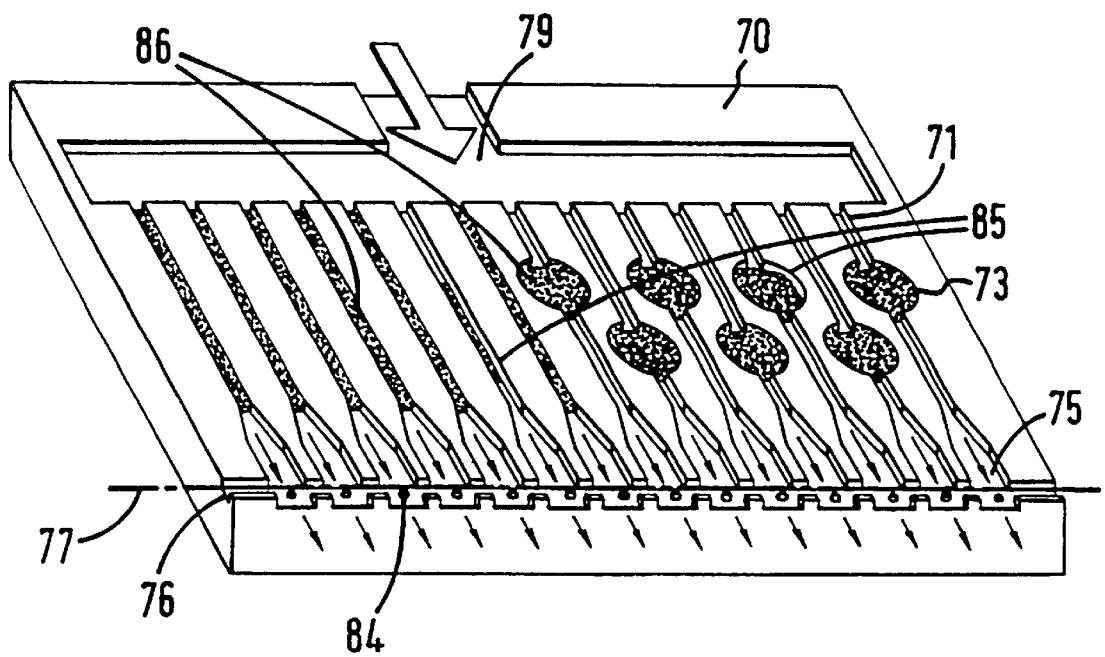
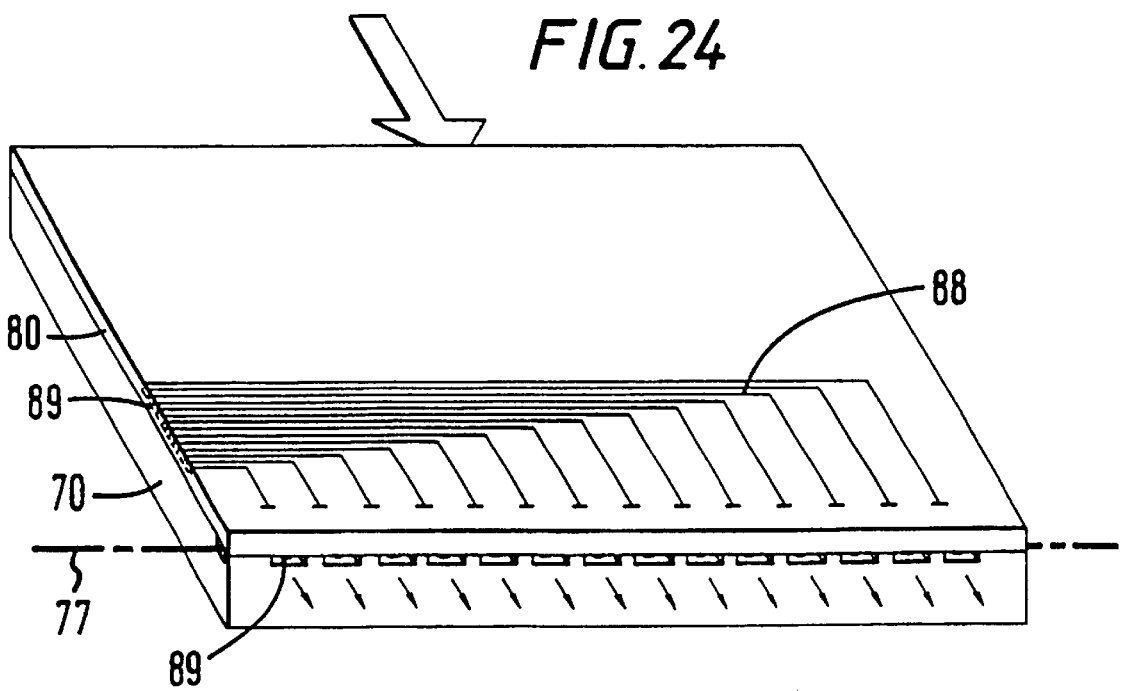

FIG. 28A
STEP 1 - Library Substrate Preparation.
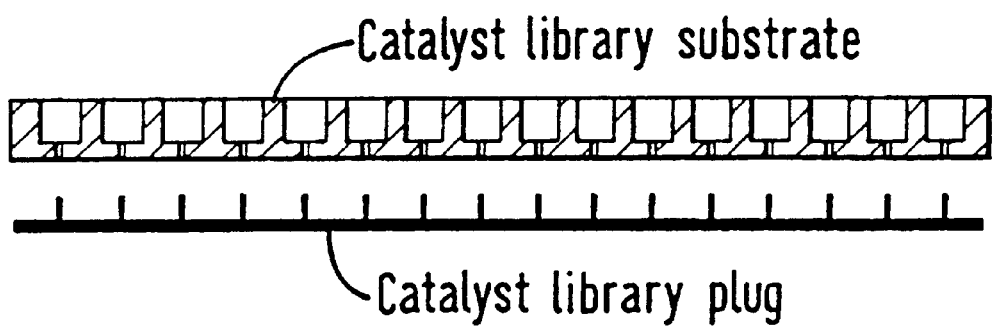
STEP 2 - Precursor Solution Deposition.
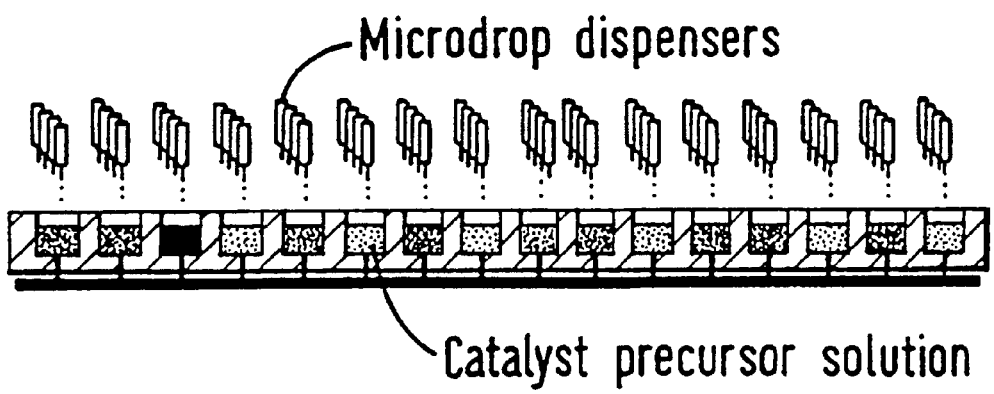
STEP 3 - Drying and Calcination.
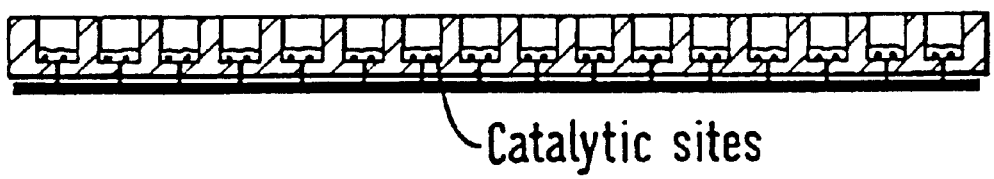

FIG. 28B
STEP 4 – Removal of the Library Plug.
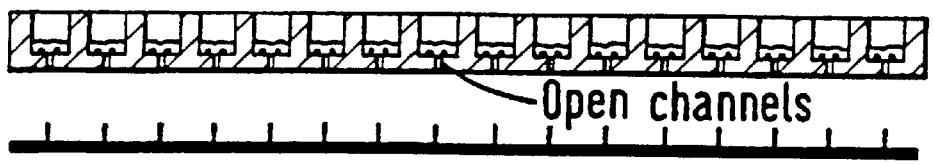
Open channels
STEP 5 – Activation.
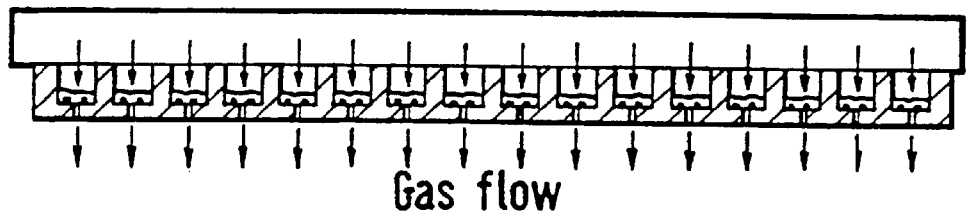
Gas flow
STEP 6 – Screening.
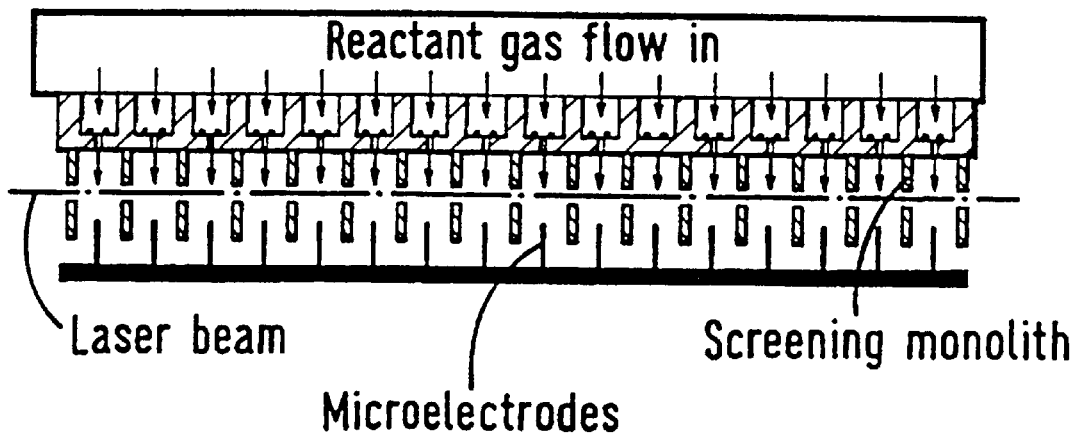
Laser beam  Screening monolith
Microelectrodes

METHOD AND APPARATUS FOR SCREENING CATALYST LIBRARIES

RELATED APPLICATIONS

This application is a continuation of International Application Number PCT/GB99/03767, filed Nov. 11, 1999, which is a continuation of U.S. Application Ser. No. 09/191,849 filed Nov. 12, 1998 now abandoned, which is a continuation-in-part of U.S. application Ser. No. 09/087,417, filed May 29, 1998, now abandoned, which is a continuation-in-part of U.S. application Ser. No. 08/949,203 filed Oct. 10, 1997, now abandoned.

BACKGROUND OF THE INVENTION

This invention relates to rapid screening for activities and selectivities of heterogeneous and homogeneous catalyst libraries by mass spectrometry. This invention provides very rapid screening of gaseous, liquid or solid products from all catalyst sites in a catalyst library by mass spectrometry and its combination with selective resonance enhanced multiphoton ionization (REMPI).

Solid and liquid catalysts are used in the manufacture of a vast array of chemicals and fuels, and in this manner significantly contribute to the economy and high living standards. National Research Council, "Catalysis Looks to the Future", National Academy Press, Washington, D.C., 1992. Catalysts also provide important environmental benefits, such as in catalytic converters for internal combustion engines. However, in spite of their significance and broad utility, the development of new and improved catalysts continues to be an arduous and rather unpredictable trial and error process. Conventionally, an individual catalyst is prepared using a large variety of tedious and time consuming methods, characterized and tested for catalytic activity, modified, again characterized and tested again, until no further improvements are justified. This approach, although time consuming, has been successful for the discovery of a significant number of solid state catalysts, Heinemann, H., "A Brief History of Industrial Catalysts", Catalysis: Science and Technology, Anderson, J. R. and Boudart, M. Eds., Chapter 1, Springer-Verlag, Berlin, 1981, and homogeneous, liquid-state catalysts, Montreus, A. and Petit, F., "Industrial Applications of Industrial Catalysts" Kluwer Publishing, New York, 1988.

Combinatorial chemistry, in which a large number of chemical variants are produced rapidly and a chemical library generated which is then screened for desirable properties using a suitable technique, is a particularly attractive approach for the discovery of new catalysts. Chem. Eng. News, Feb. 12, 1996. Combinatorial synthesis was initially used to synthesize large libraries of biological oligomers, such as peptides and nucleotides, however, the creation of small molecule libraries which can be used for drug testing is growing. Nielsen, J., Chem. & Indus., 902, Nov. 21, 1994. Recently, combinatorial diversity synthesis has been extended to solid-state compounds used in superconducting, xiang, X-D., Sun, X., Briceno, G., Lou, Y., Wang, K-A., Chang, H., Wallace-Freedman, W. G., Chen, S-W. and Schultz, P. G., "A Combinatorial Approach to Materials Discovery", Science, 268, 1738, 1995, magnetoresistivity, Briceno, G., Chang, H., Sun, X., Schultz, P. G. and xiang, X-D., "A Class of Cobalt Oxide Magnetoresistance Materials Discovered With Combinatorial Synthesis" Science, 270, 273, 1995 and luminescence, Wang, J., Yoo, Y., Takeuchi, I, Sun X-D., Chang, H., Xiang, X-D. and Schultz, P. G., "Identification of Blue Photoluminescent Composite Material from a Combinatorial Library", Science 279, 1712, 1998, Danielson, E., Golden, J. H., McFarland, E. W., Reaves, C. M., Weinberg, W. H., and Wu, X-D., "A Combinatorial Approach to the Discovery and Optimization of Luminescent Materials", Nature, 398, 944, 1997, Sun, X-D, Gao, C., Wang, J. and Xiang, X-D., "Identification and Optimization of Advanced Phosphors using Combinatorial Libraries", App.Phy.Lett., 70, 3353, 1997 and Sun, X-D., Wang, K. A., Yoo, Y., Wallace-Freedman, W. G., Gao, C, xiang, X-D. and Schultz, P.G., "Solution-Phase Synthesis of Luminescent Materials Libraries", Adv.Mater, 9, 1046, 1997. In these cases physically masked individual specimens were each measured using contact probes with a computer-controlled multichannel switching system. Microprobe sampling coupled to mass spectrometry, Kassem, M., Qum, M. and Senkan, S. M., "Chemical Structure of Fuel-Rich 1,2-$C_2H_4Cl_2$/$CH_4$/$O_2$/Ar Flames: Effects of Microprobe Cooling on Sampling of Flames of Chlorinated Hydrocarbons", Combust. Sci. Tech., 67, 147, 1989, and in situ IR, Moates, F. C., Somani, M., Annamalai, J., Richardson, J. T., Luss, D. and Wilson, R. C., "Infrared Thermographic Screening of Combinatorial Libraries of Heterogeneous Catalysts", Ind. Eng. Chem. Res., 35, 4801, 1996, have been proposed for catalyst screening, but suffer serious deficiencies in not having sufficient sensitivity, selectivity, spatial resolution or high throughput capacity to screen large catalyst libraries, as well as the lack of ability to test the activity of hundreds or thousands of compounds simultaneously. Service, R. F., "High Speed Materials Design", Science, 277, 474, 1997. Microprobe mass spectrometry requires sampling and transfer of very small quantities of gases containing low concentrations of product species from each site rendering the process impractical for rapid screening. In situ infrared techniques cannot provide information on product selectivity which is crucial for catalyst identification.

Mass spectrometry is a well established and broadly applicable method for determining mass of gaseous species. The technique involves the ionization of gaseous molecules by a number of methods, such as, for example, by electron impact or light photoionization followed by separation of ions using techniques, such as, for example, quadrupole mass spectrometry or time of flight mass spectrometry and detection of selected ions by a suitable detector. Capillary probe sampling mass spectrometry has recently been reported for screening of catalyst libraries by Cong, P.; Giaquinta, D.; Guan, S.; McFarland, E.; Self, K.; Turner, H.; and Weinberg, W. H., "A combinatorial Chemistry Approach to Oxidation Catalyst Discovery and Optimization", Process Miniaturization Section, 2nd Intl. Conf. Micro Technol., Mar. 9–12, 1998, New Orleans, La., pg. 118. Cong, et al teach introduction of reactant gas to an individual library site through an annular space surrounding a capillary tube through which product gas flows from that library site to the ionization zone of a mass spectrometer. Cong. et al report measurement of 144 library sites in about 2 hours. Sample transfer rates by capillary in the Cong, et al method are limited by the pumping speed tolerated by the mass spectrometer chamber. Another disadvantage of capillary probe sampling is the potential of adsorption and catalysis induced by relatively long transfer line surfaces. There remains a large unexplored universe of binary, ternary, quaternary and higher-order solid state materials, organometallic species and other complex metal compounds that could have superior catalytic properties. Prior conventional approaches have been inadequate to rapidly synthesize and screen this vast universe of catalytic compounds. There is clearly a need for development or more efficient and systematic methods to produce heterogeneous and homogeneous state libraries and to screen them for desired catalytic properties. Combinatorial solid state synthesis techniques have not been applied to the discovery of new and/or improved catalysts. A significant impediment for this has been the lack of a broadly applicable, sensitive, selective and high throughput measurement technique which could be used to rapidly screen large catalysts libraries. Catalyst screening requires the unambiguous detection of the presence of a specific product molecule in the vicinity of a small catalyst site on a large library, unlike superconductivity or magnetoresisitivity which can both be easily tested by conventional contact probes, or luminescence that can be tested by light emission.

SUMMARY OF THE INVENTION

This invention provides a high-throughput method to rapidly screen the activities and selectivities of homogeneous and heterogeneous catalyst libraries generated by combinatorial synthesis. Solid and liquid state catalyst libraries can be generated using a variety of techniques and can involve the combination of a large number of chemical elements and compounds.

In one embodiment, catalyst libraries may be screened for both activity and selectivity by high throughput screening using mass spectrometry. Catalyst libraries of microreactors and direct transfer of reaction products to a mass spectrometer for analysis according to this invention provides rapid screening of catalyst libraries. The technique and apparatus of this invention using catalyst libraries of an array of microreactors in monolithic structures with free jet sampling probes passing reaction products to a mass spectrometer makes it possible to screen each site in about one to five seconds, a significant improvement over the teachings of the Cong, et al reference cited above, while eliminating potential wall effects inherent in capillary microprobe sampling.

In another embodiment, the mass spectrometric analysis may also be used in combination with resonance-enhanced ionization of product gases and microelectrode screening. In cases where both screening methods are feasible, radiation activation may be used to rapidly identify promising sites and then mass spectrometry may be used to quantify yields and selectivities in greater detail. In instances in which the identification of radiation frequencies over which unique resonance enhanced multiphoton ionization signals of reaction products may not be feasible, the mass spectrometric method may be used to rapidly screen. catalyst libraries.

Detection methods in situ in the reactor use the high sensitivity, specificity and real-time features of resonance-enhanced multiphoton ionization, REMPI, in which pulsed and tunable ionizing light sources are used to selectively photoionize desired reaction products without ionizing reactants and/or other background species. Photoions or photoelectrons generated by a tunable light beam in a reaction product plume from reactants in contact with a specific catalyst library site are detected by an array of microelectrodes positioned in close proximity to the library sites. While this invention will be described using a tunable ionizing beam, any radiation beam of an energy level to promote formation of specified photoions and photoelectrons may be used. When reaction products are solids or liquids, they can be ablated using a pulsed laser beam followed by selective photoionization of the products- using a suitable UV laser. The process of this invention can provide information on catalyst selectivity by detecting several reaction product species. This can be done using different light frequencies to sequentially generate specific ions of different products and the REMPI signals can then be converted into absolute concentrations by use of calibration standards.

Internal calibration standards introduced with the reactant feed can be used to quantify reaction products, as will be readily apparent to one skilled in the art. The process of this invention is broadly applicable and can be used to simultaneously screen an entire catalyst library. The process of this invention can also be used to study operational lifetimes, resistance to poisoning, regeneration and loss of catalysts in tests or in full scale chemical plant processes.

The process of this invention for rapid screening of potential catalyst libraries for catalytic properties broadly comprises; forming a potential catalyst library having potential catalysts at a plurality of addressable sites, passing reactant gas in contact with the potential catalysts at the plurality of addressable sites, and screening gas plumes of products of reaction from the addressable sites, the screening comprising at least one of translating one of the addressable sites into a position in proximity to a sampling probe orifice followed by passing products of reaction through a free jet sampling probe to a mass spectrometer for analysis and passing a radiation beam of an energy level to promote formation of specified ions and electrons in the product stream, such as, for example, a laser beam of a frequency to promote formation of specified photoions or photoelectrons and detecting the formed photoions or photoelectrons by microelectrode collection in situ in proximity to the addressable sites.

The above advantages and other features of this invention will be better understood upon reading specific embodiments of the invention with reference to the figures wherein:

FIG. 23 is a schematic showing of an array of microreactors in a single body;

FIG. 24 is a schematic showing of another embodiment of an array of microreactors in a single body with a cover wafer;

FIGS. 28A and 28B are diagrams summarizing combinatorial catalyst library preparation and screening according to one embodiment of this invention;

Figure 31:
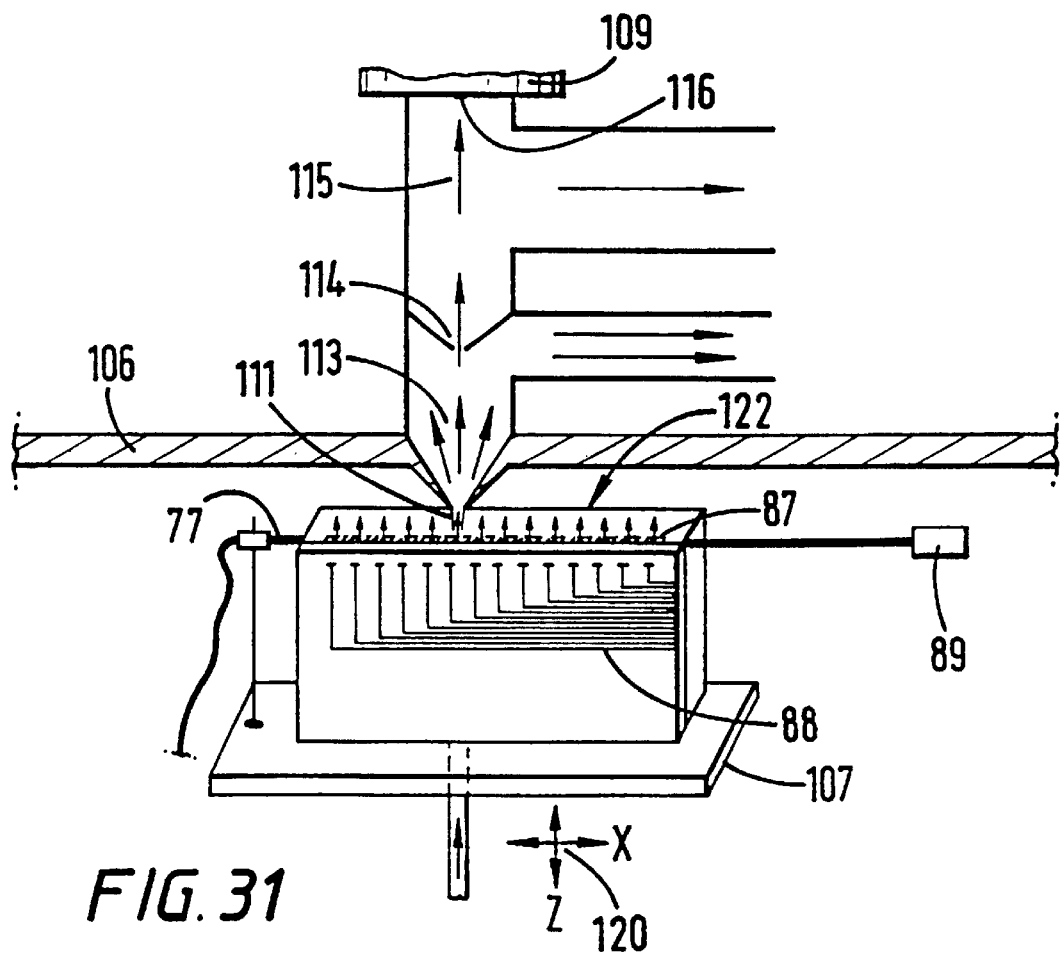
Figure 32:
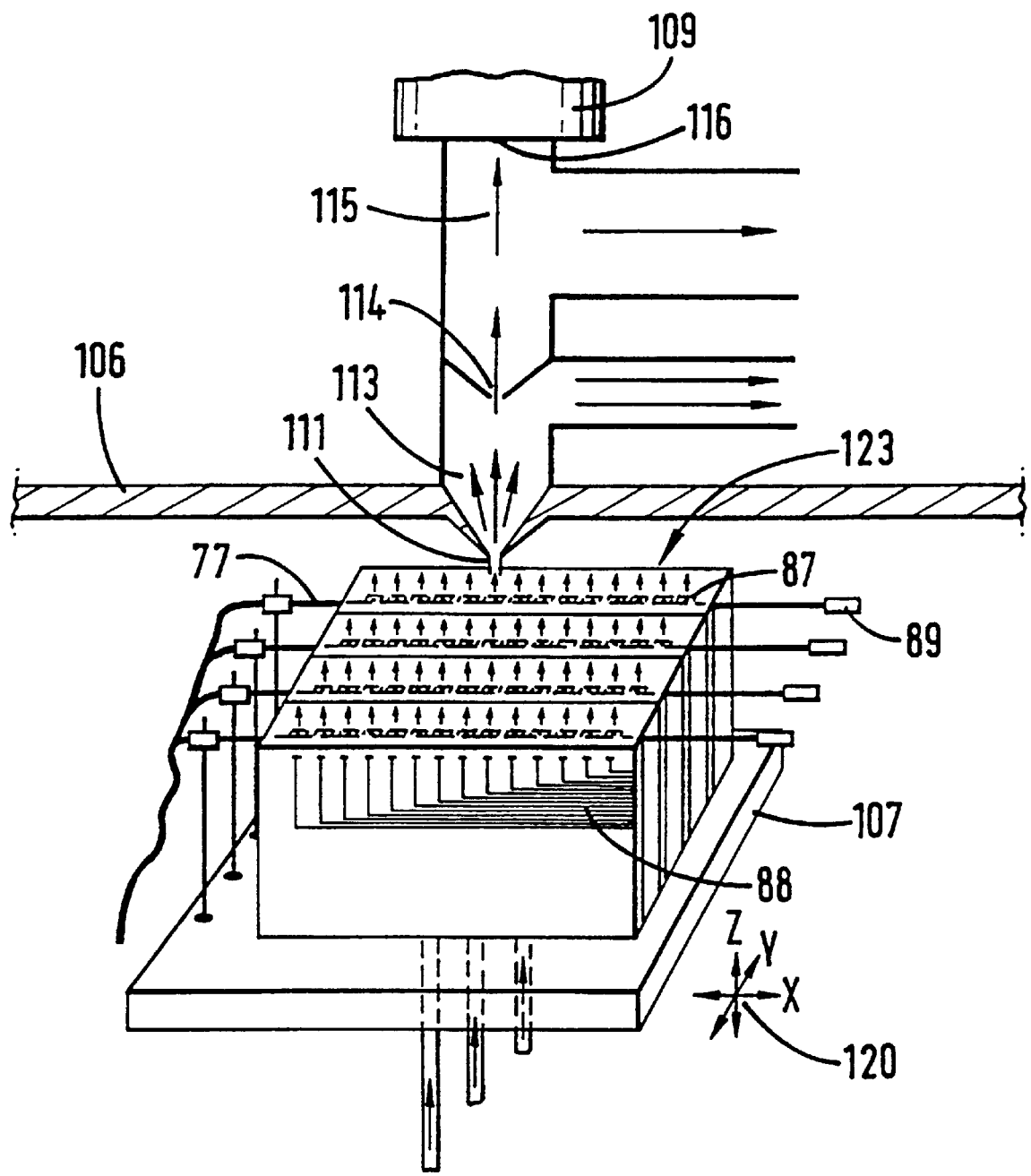

FIG. 31 is a perspective schematic showing of an array of microreactors with a sampling probe for passage of a portion of reaction products to a mass spectrometer in combination with an activating energy beam for REMPI measurement on a translation table for translation in a single dimension; and FIG. 32 is a perspective schematic showing of horizontally stacked arrays of microreactors on a translation table for translation in two dimensions for combined mass spectrometer and REMPI measurement of reaction products from a catalyst library.

DETAILED DESCRIPTION OF THE DRAWINGS

Generation of combinatorial solid state libraries has been achieved by sputtering with physical masking for measurement of superconducting, Xiang, et al, 1995, supra, magnetoresistivity, Briceno, et al, 1995, supra, and luminescence, Wang, et al, 1998, supra and Sun, et al, 1997, supra. Other thin film deposition techniques are known to the art, such as, electron beam evaporation, Danielson, et al, 1997, supra, thermal, Miyao, T., Shishikura, I., Matsuoka, M. and Nagai, M., "CVD Synthesis of Alumina-Supported Molybdenum Carbide Catalyst", Chem. Lett., 121, 561, 1996, and plasma, Kizling, M. B. and Jaras, S. G., "A Review of the Use of Plasma Techniques in Catalyst Preparation and Catalytic Reactions", Appl. Catalysis—A General, 147, 1, 1996, chemical vapor deposition, molecular beam epitaxy, Kim, Y. J., Gao, Y. and Chambers, S. A., "Selective Growth and Characterization of Pure Epitaxial $\alpha$-Fe$_2$O$_3$(0001) and Fe$_3$O$_4$(001) Films by Plasma-Assisted Molecular Beam Epitaxy, Surf. Sci., 371, 358, 1997, and pulsed-laser deposition, Gorbunov, A. A., Pompe, W., Sewing, A., Gapanov, S. V., Akhsakhalyan, A. D., Zabrodin, I. G., Kaskov, I. A., Klyenkov, E. B., Mozorov, A. P., Salaschenko, N. N., Dietsch, R., Mai, H. and Vollmar, S., "Ultrathin Film Deposition by Pulsed Laser Ablation Using Crossed Beams", App. Surf. Sci., 96–98, 649, 1996 and Russo, R. E., Mao, X. L. and Perry, D. L., "Make Catalytic Coatings by Pulsed-Laser Deposition", Chemtech, 12, 14, 1994, can be used to create large solid state catalyst libraries. These techniques provide good control of surface chemistry and are ideally suited to generate a wide spectrum of solid materials. Other well established preparation techniques, such as co-precipitation and impregnation, can also be used to generate catalyst libraries. Satterfield, C. N., "Heterogeneous Catalysts in Practice", 2nd Ed., Chap. 4, 87, McGraw Hill, N.Y., 1991. For example, a large variety of co-precipitates can be synthesized in parallel and the resulting slurries/pastes can be applied on suitable substrates using, for example, multichannel pipettes or solenoid inkjet valves to generate spatially addressable sites. Lemmo, A. V., Fisher, J. T., Geysen, H. M. and Rose, D. J., "Characterization of an Inkjet Chemical Microdispenser for Combinatorial Library Synthesis", Anal. Chem., 69, 543, 1997. Catalyst libraries can also be prepared by impregnating suitable carrier materials, such as, for example, porous silica or alumina, that were previously applied to addressable sites on a substrate by a suitable liquid solution containing a catalyst. The slurries/pastes and impregnation solutions applied on the substrates can then be dried and treated to produce suitable catalyst materials. Porous catalyst libraries can also be prepared by coating porous carriers, for example, silica or alumina, with thin films of catalytic materials using various film deposition techniques described above. An important aspect of this approach is prevention of excessive deposition to prevent pores becoming plugged by the catalytic materials. Reactant contact with the porous libraries can be accomplished either by passing reactants over or through the catalyst sites.

In testing for catalysis, however, chemical composition is not the sole determinator of activity. Physical properties of the surface, such as edges, corners and defects, as well as pore size can have an influence in determining activity. Satterfield, C. N., 1991, supra and Smith, J. M., "Chemical Engineering Kinetics", Chap. 8, 327–358, McGraw Hill, N.Y., 1981. These properties are determined to a large extent by the catalyst preparation procedure. Therefore, thin film combinatorial libraries may be subjected to a variety of treatment methods to generate suitable catalytic materials, such as, for example, oxidation, reduction, calcination, leaching, the subsequent addition of dopants and other treatments well known to the art. These different preparation processes also substantially increase the number of combinations of catalyst formulations which must be tested in order to obtain the best catalyst.

Heterogeneous catalyst libraries can also be prepared by using monolithic, or honeycomb, structures. Satterfield, C. N., 1991, supra. These materials provide parallel, uniform, straight and nonconnecting channels, thereby providing a convenient matrix for creating large catalyst libraries. A variety of cell shapes and sizes with cell densities varying from about 10 to about 500 cells per square inch can be produced with catalyst library sites. However, a wide variety of desired custom cell densities can be fabricated within and beyond the above ranges. Monolithic structures can be made from metals or they can be extruded from inorganic dough, such as magnesia-alumina silicate, through a die followed by drying and firing. Catalyst libraries can also be prepared by coating metal monoliths with inorganic substrates, wherein the metal inlay serves as a barrier to prevent intercell diffusion of species. Catalysts can then be incorporated into the library substrate using any of the variety of methods described above. Monolith structures can also be machined for optical access and placement of microelectrodes.

Homogeneous catalyst libraries comprising, for example, organometallic and inorganometallic compounds and other complex molecules such as enzymes, can be similarly generated using multichannel pipettes, Burgess, K., Lim H-J., Porte, A. M. and Sulikowski, G. A., "New Catalyst and Conditions for a C-H Insertion Reaction Identified by High Throughput Catalyst Screening", Angew. Chem. Int. Ed. Engl., 5, 220, 1996, and solenoid inkjet valves. These libraries may have arrays of microtubes bundled together with reactant gas bubbled through them. Homogeneous liquid catalysts can also be held or immobilized in the pores of porous carriers which can be in the form of particles or can be coated on the walls of monolithic structures. Since the screening method of this invention can be readily miniaturized, the physical dimensions of catalyst sites that determine library density are primarily dependent upon the nature of the catalyst, liquid or solid phase, the method of preparation of the library, diffusional mixing of gases in the library, heat conduction through the library substrate, the objectives of the screening process and other relevant factors. For example, when the objective of screening is to evaluate catalytic materials for gas-phase reactions using flat catalytic sites, library densities will be limited by the gas-phase diffusion because at high library densities intersite diffusion can result in signal crossovers between sites. However, the evaluation of catalyst operating temperature windows requires the fabrication of libraries in which each site is thermally insulated to maintain different temperatures. In this case, the library density will be limited by the thermal conductivity of the wafer of substrate. For liquid phase homogeneous catalysts, surface tension and viscosity play a significant role in determining gas dispersion, and thus in establishing the minimum dimensions of the library sites and hence the library density.

In this invention, the catalyst sites must be sufficiently separated from each other so that product formation from each site and its unambiguous detection can be achieved. Monolithic, or honeycomb, structures offer advantages by providing clear physical separation of the library sites. These and other catalyst library design factors will be further discussed in descriptions of screening methods. Unambiguous and rapid screening of solid catalyst sites of 0.5 cm by 0.5 cm have been demonstrated using the present invention. These site dimensions provide catalyst libraries having densities of about 10 sites per square inch which permits creation of over 900 sites on a substrate having dimensions of 8.5 inches by 11 inches, the size of a sheet of letter paper. Higher library densities are clearly practical using smaller site dimensions or by the use of monolithic structures. The pattern of the sites should be designed to expedite the generation and screening of the libraries, libraries having rows of catalyst sites offering distinct advantages both for generation and screening of the sites. Any method of production of chemical libraries having sites of the above mentioned characteristics is suitable for production of catalyst libraries for use in the rapid screening process for catalyst evaluation according to this invention.

Figure 29:
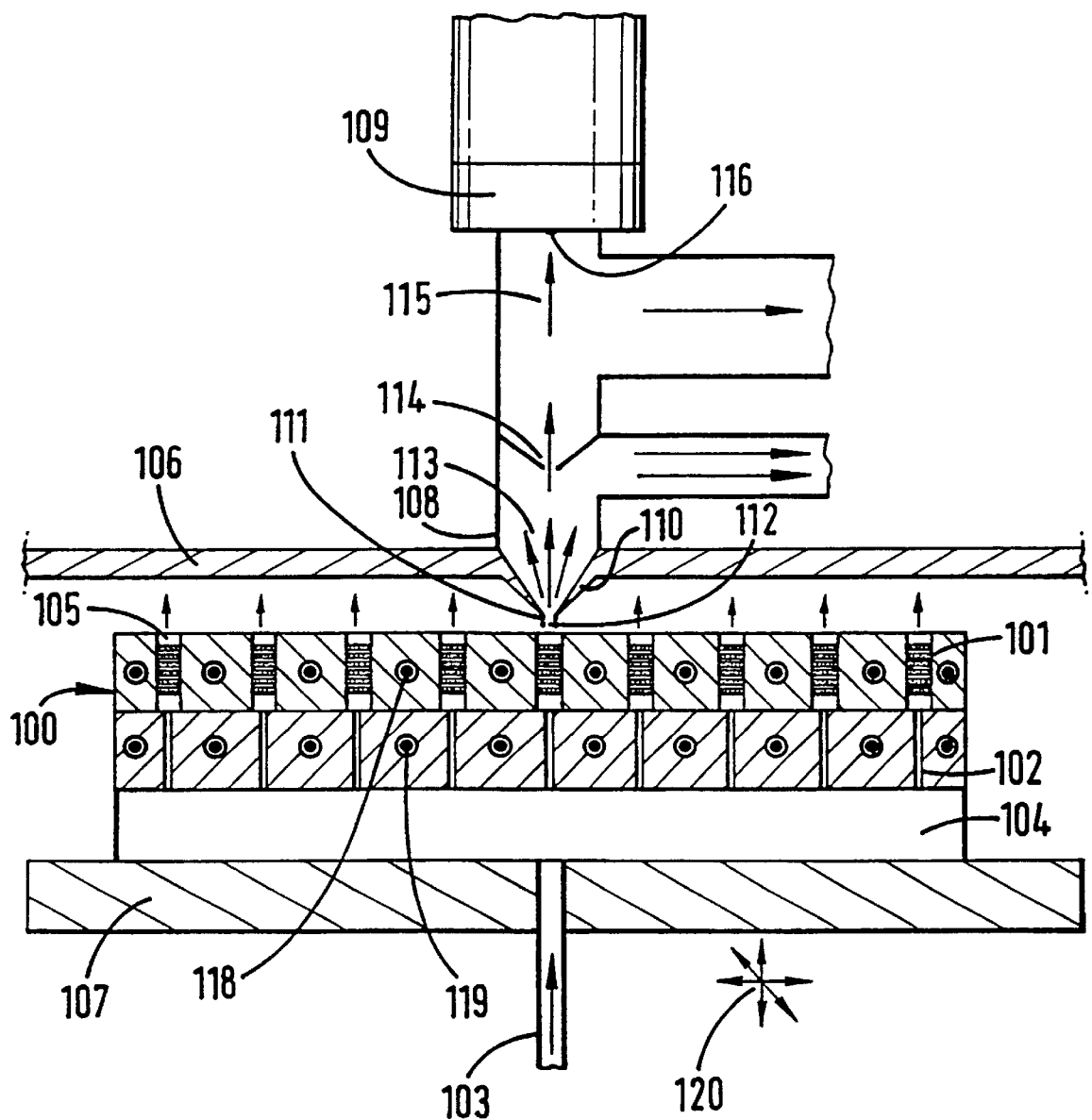
FIG. 29 is a cross sectional schematic showing of a sampling probe having a conical orifice in sampling mode for transfer of reaction products of one site in a catalyst library in an array of microreactors to a mass spectrometer for analysis.

In one embodiment of this invention, sampling of reaction products emanating from individual sites in a library is accomplished by passing the reaction products through a small orifice, placed in close relationship to the source of the reaction products, to a significantly larger cross section area chamber for passage to a detection device, such as, a mass spectrometer. Shown schematically in FIG. 29 is a catalyst library having individual sites configured in microreactors, as will be described below in further detail. Briefly, inert microreactor body 100 has reactant feed passages 102 leading to enlarged catalyst zones with catalyst beds 101. Reactant gases are supplied through reactant gas supply passage 103 to reactant gas distribution plenum 104 for distribution to reactant feed passages 102. Reaction products exit the microreactors through reaction products exit passages 105 and pass from reactor enclosure 106 or a portion may pass from an individual library site through a micro sampling probe to a detection device. The reactor enclosure can be pressurised to provide the desired reaction pressure. Alternatively, each microreactor can be individually pressurised to test catalysts under different pressures, or each array of microreactos can be individually pressurised. As shown in FIG. 29, the catalyst library is fixidly mounted on translation table 107 for positioning of sampling probe 108 over a single library site for detection of reaction products from that site. Translation table 107 may be moved in x-y-z directions by computer controlled stepper motors, as well known by one skilled in the art, to rapidly move single library sites into position for sampling from a single site by sampling probe 108 fixidly mounted in reactor enclosure 106. It is also possible to translate the sampling probe and the detection system while maintaining the library stationary, or both the library and the sampling probe may be simultaneously moved by translators. As shown in FIG. 29, a single library site has been moved to a sampling position in proximity to sampling probe 108 to pass a portion of reaction product gases through the sampling probe to mass spectrometer 109. Reactants may be passed through all library sites may be operated simultaneously and product gases from other library sites may be withdrawn from reactor enclosure 106. Following product gas analysis at a particular library site, the library may be translated into position for evaluation of another catalyst site. Since several or all of the sites in a library may be under reaction conditions simultaneously, analysis of the reaction products may take place immediately after positioning the library without the necessity of waiting for equilibrium conditions and without transfer line delays encountered by use of capillary tube sampling probes, as described by Cong, et al, supra.

The tip of sampling probe 108 must be made from material which can be machined and withstand the pressure and temperature of the reaction chamber, in the event that the reactor enclosure 106 is pressurised, as well as being inert to the reactants and reaction products. As shown in FIG. 29, reactor enclosure wall 106 has sampling cone 110 which may be integral with or attached with proper sealing to the reactor enclosure wall. When the microreactors in the reactor array are internally pressurised and products discharged into atmospheric pressure, the sampling cone can be directly attached to the mass spectrometer. As shown, sampling cone 110 has a sampling probe extension 111 to minimally perturb the reaction product stream and allow positioning of the sampling probe very close to the catalyst reaction site without hindering product gas venting. Sampling cone 110 should have a half cone angle of about 15 to about 45 degrees to allow free jet expansion of the gas samples into a vacuum chamber while sampling probe extension 111 may have a smaller cone angle. Free jet expansion in the sampling probe 1 eads to substantial cooling and quenching of all possible homogeneous and heterogeneous reactions and provides direction to the molecules towards a mass spectrometer positioned downstream of the sampling cone. Sampling cone orifice 112, at the small end of the cone, is sized so that reaction chamber pressures and vacuum pump capacities of all stages can be accommodated. Suitable sampling cone orifice diameters are about 1 micrometer to about 200 micrometers, typically about 5 micrometers to about 50 micrometers for use with modest size vacuum pumps. The expanding reaction product sample from the sampling cone passes through first vacuum stage 113 and skimming cone 114 to ensure that only the central portion of the reaction product sample jet enters the mass spectrometer chamber, eliminating any surface induced reactions that may occur in the sampling probe. The cone angle and diameter of the opening at the tip of the skimmer must be suitable to meet reaction chamber pressure and sampling probe pumping speed requirements, as can be readily determined by one skilled in the art. The reaction product sample jet passing through the skinning cone then passes through second vacuum stage 115 and is directly introduced into a mass spectrometer through mass spectrometer inlet orifice 116. The mass spectrometer can be a quadrupole mass spectrometer or a time of flight spectrometer with fast electronics to acquire and process the data, as well known to the art. Electron impact or radiation can be used to ionize species. Tunable lasers can also be used to selectively ionize reaction products under REMPI conditions. When catalyst libraries are screened at atmospheric pressure, or when microreactor arrays are internally pressurised and products discharged to atmospheric pressure, only one pump down stage may be necessary to prepare the sample for mass spectrometer pressure conditions, while catalyst libraries screened at high pressures may require more than two pump down stages, as will be apparent to one skilled in the art. The staged pump down process rapidly brings the pressure of the reaction products from high pressures, in some applications from about 20 to about 50 atmospheres, to a small fraction of an atmosphere so that the reaction product samples can be directly introduced into the mass spectrometer where pressures are typically maintained at about $10^{-5}$ to about $10^{-6}$ Torr. When microreactors in an array are internally pressurised and discharged into atmospheric pressure, this will constitute a pump down stage. The pressure of the last pump down stage, second stage in FIG. 29, and the mass spectrometer inlet orifice diameter must be compatible with this pressure limitation in view of the pumping speed attainable by the vacuum system. Typically, pressure in the first and second stages of a two stage system should be maintained at about 760 to about $10^{-2}$ and $10^{-2}$ to about $10^{-5}$ Torr, respectively. The pressures in all stages should be maintained the same during calibration and screening processes to quantify the results of catalyst evaluation.

The distance from the sampling probe orifice to the mass spectrometer should be kept as short as possible to maximize detection sensitivity since the gas concentration decreases upon expansion into vacuum according to $1/r^2$, where r is the distance from the tip of the sampling probe. However, shorter sampling probe orifice to mass spectrometer distance decreases the pumping speed provided by the vacuum pump(s), thereby adversely affecting the free jet sampling process. In view of these conflicting results, the spacing between the sampling probe orifice and the mass spectrometer is determined to balance signal detection and pumping speed needs. Typically, spacing between the sampling probe orifice and the mass spectrometer is about 7.5 to about 25 cm. In the limit, the sampling system performance approaches molecular beam sampling conditions as described by Chang, W. D.; Karra, S. B.; and Senkan, S. M., Molecular Beam Mass Spectroscopic Study of Trichloroethylene Flames, Environ. Sci. Technol., 20, 12, 1243, (1986) where the expanding sample jet velocities in the first stage can reach supersonic levels and the jet stream entering the mass spectrometer is a directed molecular beam.

Figure 30:
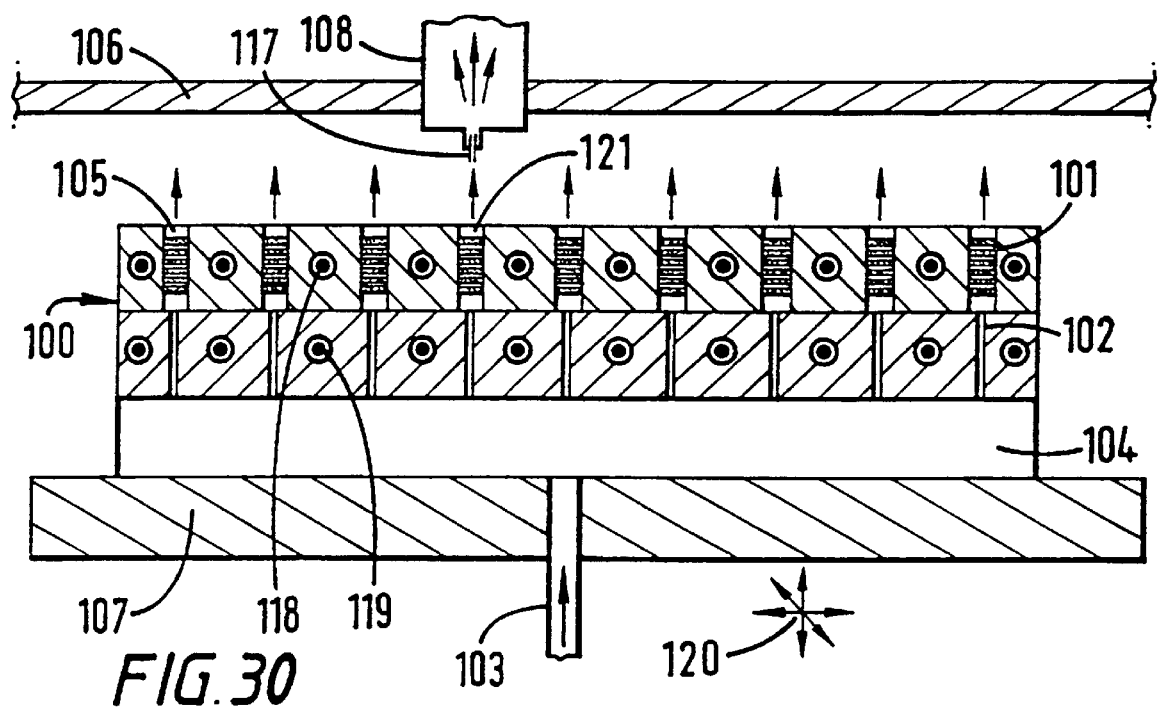
FIG. 30 is a schematic showing of a sampling probe similar to FIG. 29 having a capillary orifice in a translation mode.

Another embodiment of the invention is shown in FIG. 30 wherein the microreactor array catalyst library is shown in translation mode withdrawn from the sampling position shown in FIG. 29 and sampling orifice 117 is a short capillary inert to reactants and reaction products having a diameter of about 1 to about 500 micrometers, typically about 5 to about 100 micrometers, and lengths of about 1 micrometer to about 20 cm, typically about 5 to about 100 micrometers. The capillary orifice used in this invention is significantly shorter than those used by Kassem, M., Qum, M., and Senkan, S. M., supra, and by Cong, P., Giaquinta, D., Guan, S., McFarland, E., Self, K., Turner, H. and Weinberg, W. H., supra. To maximize product sample signals and to minimize pumping speed requirements, capillary diameters of about 5 to about 20 micrometers and capillary lengths of about 50 to about 100 micrometers are compatible with small commercial vacuum pumps. The capillary orifice of this embodiment passes directly into first vacuum stage 113 of sampling microprobe 108. In other respects, the apparatus and process shown in FIG. 30 is similar to those described above with respect to FIG. 29.

In the sampling probe configurations shown in FIGS. 29 and 30, the time required to transfer reaction products from the reaction zones of the microreactors to the mass spectrometer can be in the order of microseconds to tens of milliseconds. Acquisition of mass spectrometric data can be accomplished in a time scale of the order of several hundred milliseconds, especially when specific mass ions are monitored. Therefore, the time limiting step of the screening process is the time to mechanically position individual sites in the library in sampling position, in proximity to the sampling orifice of the sampling probe, by the stepper motor driven translation apparatus. All microreactor sites in the catalyst library can be simultaneously operated to simultaneously generate reaction products. In this mode, the product stream from any site in the library can be sampled at any time without the requirement of waiting for establishment of steady state operating conditions in each site. Alternatively, reactant gas flows to individual sites in a library may be independently controlled by flow controllers in each reactant feed passage so that reactant flow to a specific library can be turned on early enough for establishment of steady state operating conditions while screening another site and then turned off after the screening process of that site, as more fully explained below. This mode of operation is necessary when it is important to screen the library sites at the same on-stream time conditions.

The catalyst library shown in FIGS. 29 and 30 represent a cross section of an array of packed bed microreactors in a high thermal conductivity metal microreactor body. Catalyst powders, particles, or any other form of solid catalysts, can be placed into cylindrical, or other shaped, cartridges which can be inserted into the catalyst zones of the microreactor body. Other methods of catalyst loading of microreactors, as more fully explained below, are also suitable. Reactor heating elements 118 are shown embedded in microreactor body 100 to provide uniform temperature control of the entire library. Individual library sites also may be insulated from each other and each have an individually controlled heating element to provide different temperature control of each site. In a similar manner, each site may be provided with an individual flow control regulator to provide different residence times in each site. A similar reactant preheat zone in the reactant feed zone may be provided, as shown by reactant preheating elements 119, to heat reactant gases to a desired temperature prior to contact with the catalyst. These microreactor configurations are more fully described below. The entire library is attached to translation table 107 in a fixed relation to provide precision x-y-z three dimensional movement, as indicated by translation arrows 120. Two dimensional translation in the x and y axes moves the library into position for sampling a specific site while movement in the third dimensional z axis positions reaction product exit passage 121 into proximity to sampling cone orifice 112 of sampling microprobe 108.

The mass spectrometric screening method described above can be used with other catalyst library designs, such as, for example, those described herein as well as other types of libraries which may include homogeneous catalyst libraries, fluidized bed (gas and liquid) libraries, and combinations thereof The mass spectrometric screening method may be combined with the resonance-enhanced multiphoton ionization method, REMPI, described in greater detail herein. The REMPI method for screening catalyst libraries has been more fully described in Senkan, S. M.; High-Throughput Screening of Solid-State Catalyst Libraries, Nature, 394, 350, Jul. 23, 1998. The combination of mass spectrometric screening, as described above, with a microreactor array as shown in and described further in respect to FIG. 24 is shown in FIG. 31. As shown in FIG. 31, microreactor array 122 has activating radiation beam 77 passing through the reaction product streams from the individual sites with microelectrodes 87 in proximity thereto with internal wiring leads 88 for powering each electrode and for passage of detection signals from each electrode to a detection device. In the manner as described above with respect to FIG. 29, sampling cone tip 111 with a sampling orifice is placed in proximity to the reaction product stream at the exit of an individual microreactor by movement of the microreactor array on translation table 107 in an x direction and placed in sampling position by movement of the microreactor array in a z direction, as indicated by translation arrows 120.

Figure 25:
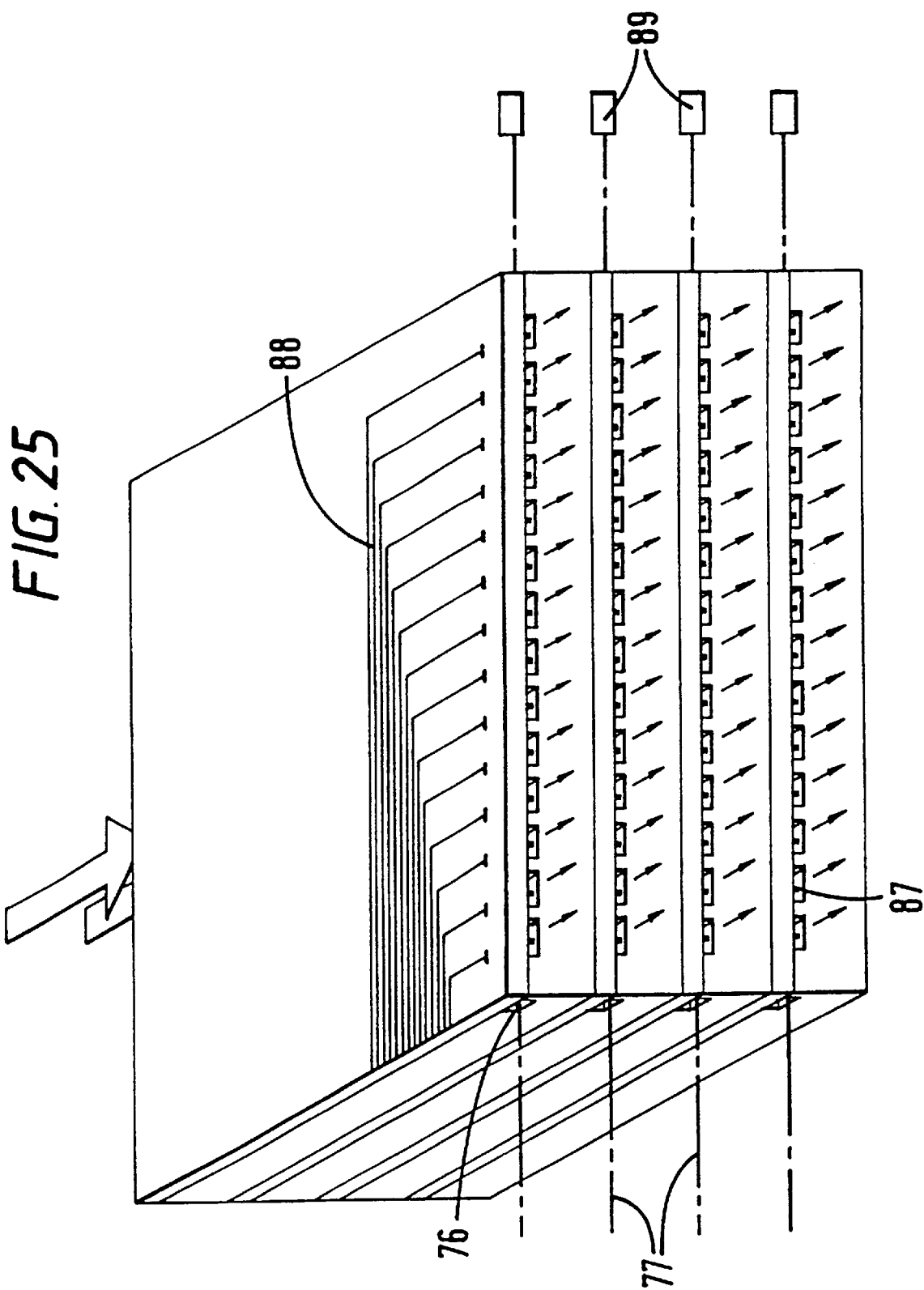
FIG. 25 is a schematic showing of a catalyst library in vertical stacked arrays of microreactors as shown in FIG. 24.

Stacked arrays of microreactors for combined mass spectrometric and REMPI screening methods may be formed using multiple microreactor arrays, as more fully shown in and described with respect to FIG. 25. As in the case of reactor arrays shown in FIGS. 29 and 30, heating elements can be embedded in thermal conducting walls between individual microreactors. In similar manner as shown and described with respect to FIG. 31, REMPI measurements and/or mass spectrometric measurements may be made by positioning the arrays to a single site for mass spectrometric sampling by movement of translation table in the x-y-z axes indicated by translation arrows 120. Fiber optics facilitates mounting laser light sources on translation table 107 to provide laser beams 77 to all of the library sites simultaneously for rapid REMPI microelectrode screening. In cases where both methods of screening are feasible, radiation activation may be used to rapidly identify promising sites and mass spectrometric analysis used to quantify yields and activities more precisely.

It will be apparent to one skilled in the art upon reading of this description that any of the microreactor configurations, microreactor arrays, and stacked arrays of microreactors disclosed with respect to the REMPI microelectrode screening method may be readily adapted to the mass spectrometric screening method by mounting the microreactors on a suitable translation table and provision of a free jet expansion sampling probe leading to a mass spectrometer.

Screening of large libraries for desired catalytic activity according to this invention is based upon the fact that when a laser frequency is tuned to a real electronic intermediate state of a gaseous molecule, the cross section for ionization of that molecule is significantly enhanced. This process is resonance-enhanced multiphoton ionization, or REMPI. When the laser wavelength is not tuned to a real electronic state, the probability for photoionization is very small. Thus, the ionization cross section reflects the absorption-excitation spectrum of the intermediate electronic state of the molecule. Using REMPI, specific catalytic reaction products can be selectively ionized with high efficiency using a suitable laser frequency, while avoiding the simultaneous photoionization of reactants and/or background gases. While preferred embodiments of this invention are described using laser beams, any radiation beam of a suitable energy level to promote formation of specified ions and electrons from reaction products may be used, thereby allowing detection of the formed ion and/or electrons by microelectrode collection in downstream proximity to the radiation beam.

In cases where the catalytic reaction product(s) do not provide easy generation of REMPI photoions, the process of this invention may be used in detection of directly related products. For example, reaction product molecules may be fragmented into smaller daughter products by a suitable energy source, such as, for example, a pulsed laser beam or by a plasma arc. The fragments may be stable molecules, radicals or ionic species. Following fragmentation of a catalytic reaction product molecule to a daughter product which can be uniquely attributed to a catalytic reaction product molecule that is desired to be detected, the daughter product can be selectively photoionized using the REMPI process and detected by a microelectrode as described herein. Quantification of reaction products by detection of their fragmentation products requires additional calibration to account for the efficiencies of fragmentation.

It may also be possible that upon irradiation of reaction products by specific light frequency, the reaction products or their fragmentation products may emit unique radiation signatures involving, for example, luminescence, fluorescence or phosphorescence. These emissions can then be used to rapidly screen the catalyst libraries using, for example, monochromators and diode array and charge coupled device (CCD) detectors.

For example, selective identification of ethylene oxide ($C_2H_4O$) and acetaldehyde ($CH_3CHO$) as a consequence of the reaction of ethylene ($C_2H_4$) and ($O_2$) can be performed on fragmentation products which may be described by the following equations:

$$C_2H_4O + h\nu \rightarrow CH_2O + CH_2$$

$$C_2H_4O + h\nu \rightarrow C_2H_4 + O$$

$$C_2H_4O + h\nu \rightarrow C_2H_3 + OH$$

In the case of acetaldehyde, the fragmentation may be described by the following: $CH_3CHO + h\nu \rightarrow CH_3 + CHO$ Although it may be possible to detect the catalytic product molecules directly by their REMPI ions, information about their presence in a reactant-product mixture can also be obtained by measuring the REMPI characteristics of their fragmentation products. Thus, the formation of fragmentation products $CH_2O$, $CH_2$, $C_2H_3$, O and OH can be uniquely attributed to ethylene oxide while the formation of $CH_3$ and CHO can be uniquely attributed to acetaldehyde. In this manner, the selective detection of any one of the fragmentation products, except ethylene which is present abundantly as a reactant, can signify the level of the parent ethylene oxide and/or acetaldehyde in a mixture of these chemicals.

As another example, acrylonitrile ($C_2H_3CN$) when produced by the reaction of propane ($C_3H_8$), ammonia ($NH_3$) and oxygen may be detected by detection of either of the products resulting from the fragmentation $C_2H_3CN + h\nu \rightarrow C_2H_2 + CN$ which gives unique information about the level of acrylonitrile in a product mixture.

There are several means for inducing REMPI, the most common is the resonant 2-photon ionization, R2PI, in which one photon, $h\nu_1$, energizes the molecule to an excited electronic state and the second photon, $h\nu_2$, ionizes the molecule. Lubman, D. M., "Lasers and Mass Spectrometry", Oxford Univ. Press, New York, 1990, Chap. 16, Lubman, D. M. and Li, L., "Resonant Two-Photon Ionization Spectroscopy of Biological Molecules in Supersonic Jets Volitalized by Pulsed Laser Desorption", 353. However, depending upon circumstances, the absorption of two or more photons in each step can also be used for REMPI. Ionization occurs if $(h\nu_1 + h\nu_2) > IP$, where IP is the ionization potential. The two photons used can have the same or different energies and can be obtained from the same or different lasers. Higher energy UV photons may also be used to photoionize species in a single photon process. The two photon REMPI process can be described for selective photoionization of a product P by the following equations: $P + h\nu_1 = P^*$ and $P^* + h\nu_2 = P^+ + e$, wherein P is the product, $P^*$ is the real electronic excited state of the product, $P^+$ is the photoion of the product and e is the photoelectron. By varying the photon energies, which can be accomplished using tunable lasers, the ionization spectrum of the target molecule P can be mapped to determine a suitable laser frequency which can be used to exclusively ionize it without simultaneously ionizing other molecules in the mixture. Since the REMPI process involves the participation of two or more photons, the laser light wavelengths used must take this into account. As a crude approximation, each photon in a successful REMPI must possess an energy of about ½ the IP in the R2PI process using a single laser beam. Similarly, if a single laser beam is used, each photon energy must be about ⅓ the IP in a 2+1 process and ¼ the IP in a 2+2 process, etc. When two or more laser beams are used, each photon energy can be independently selected to optimize the resulting REMPI signals. Laser wavelengths covering the range from deep ultraviolet, UV, such as 150 nanometers, nm, to visible light, such as 700 nm, can be used to induce REMPI using a variety of multiphoton processes.

REMPI is inherently a high resolution technique in which ion absorption features of any molecule can be determined with high precision. Also, molecules are ionized from a vibrational level of an electronically excited state, thereby providing specific photoionization of only target molecules. This can be used to distinguish between isomers, for example dichlorotoluenes, due to their different electronic structures. Zimmerman, R., Lerner, Ch., Schramm, K. W., Kettrup, A. and Boesl, U., "Three-dimensional Trace Analysis: Combination of Gas Chromatography, Supersonic Beam UV Spectroscopy and Time-of-Flight Mass Spectrometry", Euro. Mass Spectrom., 1, 341, 1995. The REMPI process can be sequentially used to detect different products using different laser frequencies, thus also providing the determination of catalyst selectivities. REMPI is a high sensitivity technique with real-time detection of species at low parts per billion, Gittins, C. M., Castaldi, M. J., Senkan, S. M. and Rohlfing, E. A., "Real-Time Quantitative Analysis of Combustion Generated Polycyclic Aromatic Hydrocarbons by Resonance Enhanced Multiphoton Ionization Time of Flight Mass Spectometry", Anal. Chem., 69, 287, 1997, and high parts per trillion already demonstrated. Castaldi, M. J. and Senkan, S. M., "Real-time Ultrasensitive Monitoring of Air Toxics by Laser Photoionization Time of Flight Mass Spectrometry, J. Air and Waste Mgmnt. Assoc., 48, 77, 1998.

Figure 1:
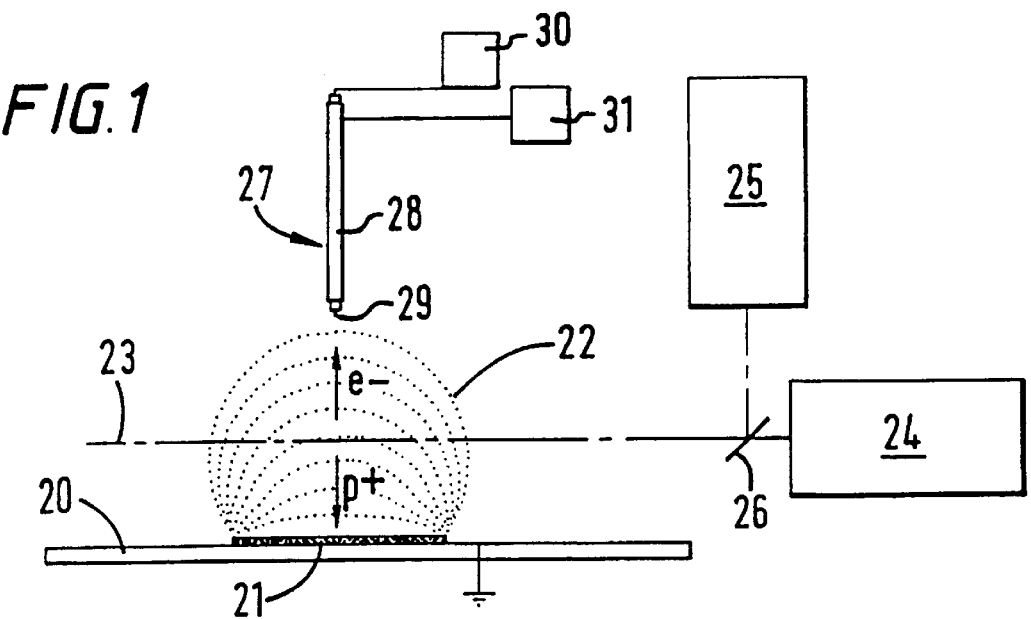
FIG. 1 is a schematic showing the principles of REMPI microelectrode detection of product species.

FIG. 1 is a generalized illustration of the REMPI method of selective detection of a gaseous product generated by contacting a catalytic site with reactants. According to the present invention, gaseous reaction products form a gaseous plume 22 when catalyst 21 mounted on substrate 20 is contacted by the reactants. The gaseous products are photoionized by pulsed UV laser beam 23 formed from tunable laser source 24 and/or using second tunable laser source 25 directed by mirror 26 through the central portion of gaseous product plume 22 generating photoions, $P^+$, and photoelectrons e, as indicated in FIG. 1. Microelectrode 27 is positioned a few millimeters above laser beam 23 to collect the photoelectrons or photoions, depending upon the voltage bias applied by DC power source 30 to cathode 28 and anode 29. The electrical signal collected by microelectrode 27 is then amplified and detected by detector 31, such as a digital oscilloscope. If the measured electrical signal is higher than reference sites which do not have catalysts, the site can be tagged catalytically active. Otherwise, the site must be considered catalytically inactive. It is apparent that selection of a suitable laser frequency, or frequencies for detection of multiple products, is critical to ensure that the electrical signals generated by the laser beam are exclusively due to photoionization of the specified product gas and not from the reactants and/or background gases. The suitable laser frequency for a specific material may be identified by laser photoionization mass spectrometry studies, using for example, a tunable laser and time-of-flight mass spectrometer. Castaldi, M. J. and Senkan, S. M., 1997, supra and Gittins, C. M., Castaldi, M. J., Senkan, S. M. and Rohlfing E. A, 1998, supra. Using this approach, a gas mixture containing the species of interest is introduced into a vacuum chamber using, for example, a pulse valve. The expanding gas jet is then intercepted by UV photons at a specific energy from a tunable laser generator. The resulting REMPI signals are then recorded by the time-of-flight mass spectrometer system. By scanning the UV laser frequency range, the photoionization spectra of the reactants, products, by-products and background gases can be determined. In the case of molecular isomers, the photoionization spectra of each isomer must be determined individually. Following the determination of the photoionization spectra for all of the relevant species, specific UV frequencies can be identified which would lead to the exclusive generation of the REMPI ions of specific product isomers desired to be evaluated.

It should be recognized that the REMPI spectra broadens at elevated temperatures due to the overlapping transitions from a large number of rovibronic levels. However, it is generally possible to identify a laser frequency that selectively photoionizes the desired products without interferences from the reactants, other products and the carrier gas, due to the availability of broadly tunable UV lasers. This identification process is expedited when the product gases are structurally different from the reactant and background gases, for example, in the production of benzene, an aromatic compound, from hexane, an aliphatic compound, in Ar carrier gas with $H_2$ as the only by-product. Potential problems associated with spectral congestion of REMPI signals can be effectively solved by the use of supersonic jet expansion. Parker, D. H., "Laser Ionization Spectrometry and Mass Spectrometry" in "Ultrasensitive Laser Spectroscopy" Kliger, D. S. Ed., Academic Press, New York, 1983 and Trembreull, R., Sin, C. H., Li, P., Pang, H. M. and Lubman, D. M., "Applicability of Resonant Two-Photon Ionization in Supersonic Beam Mass Spectrometry to Halogenated Aromatic Hydrocarbons", Anal. Chem., 57, 1186, 1985. Jet expansion, which can be achieved by expanding the product gases into a vacuum through a small orifice, leads to transitional, rotational and vibrational cooling resulting in significant simplification of the REMPI spectra. This method permits selective detection of specific species in a similar background.

The product photoions and photoelectrons generated above the catalyst site can be collected using a microelectrode, which can be either anode or cathode or both. The substrate upon which the catalyst library is deposited can also serve as the cathode or the anode, or another microelectrode can be placed within the substrate for this purpose. High temperature REMPI-electrode approach has previously been used to determine the concentration of gaseous species containing only a few atoms, such as PO, NO, H and O. Smyth, K. C. and Mallard, W. G., "Two Photon Ionization Processes of PO in a $C_2H_2$/air Flame", J. Chem. Phys., 77, 1779, 1982; Cool, T. A., "Quantitative Measurement of NO Density by Resonance Three-Proton Ionization", App. Optics, 23, 10, 1559, 1984; Goldsmith, J. E. M., "Resonant Multiphoton Optogalvanic Detection of Atomic Oxygen in Flames", J. Chem. Phys., 78(3), 1610, 1983; and Bjorklund, G. C., Freeman, R. R. and Storz, R. H., "Selective Excitation of Rydberg Levels in Atomic Hydrogen by Three Photon Absorption", Optics Comm., 31(1), 47, 1979. These earlier studies, which exhibit problems of spectral congestion and broadening of REMPI signals, implicitly teach against use of the REMPI-electrode approach when larger molecule species are involved. However, it has now been discovered that larger molecules can be measured by this technique for catalyst screening. Significant broadening of the REMPI spectra can be tolerated in catalyst screening where the REMPI features of the reactants and products are generally separated. When the REMPI spectra overlap, which should be rare in catalyst screening where reactants and products have distinct electronic structures, this problem can be solved by jet cooling the products by expanding them into a vacuum chamber through small orifices.

The REMPI microelectrode technique can also be used to detect liquid and solid products. In these cases, the reaction products must be gasified first using an ablation laser, for example, a pulsed $CO_2$ or another type of laser. The gasified products then can be photoionized by REMPI and detected by a microelectrode, as described above. The REMPI method can also be used to monitor reaction intermediates involved in the catalytic process, which cannot be detected by analysis of product gases collected at the exit of the reactor. This can be particularly useful in developing insights into reaction pathways associated with catalytic reactions, and thereby can significantly accelerate the catalyst development process No literature is known to the inventor which suggests the use of REMPI and microelectrodes for the high speed screening of heterogeneous and homogeneous catalyst libraries. A multitude of approaches for the rapid screening of large libraries for catalytic activity may be followed, and the following presently preferred approaches are set forth as exemplary and should not be considered as limiting the invention.

Figure 2:
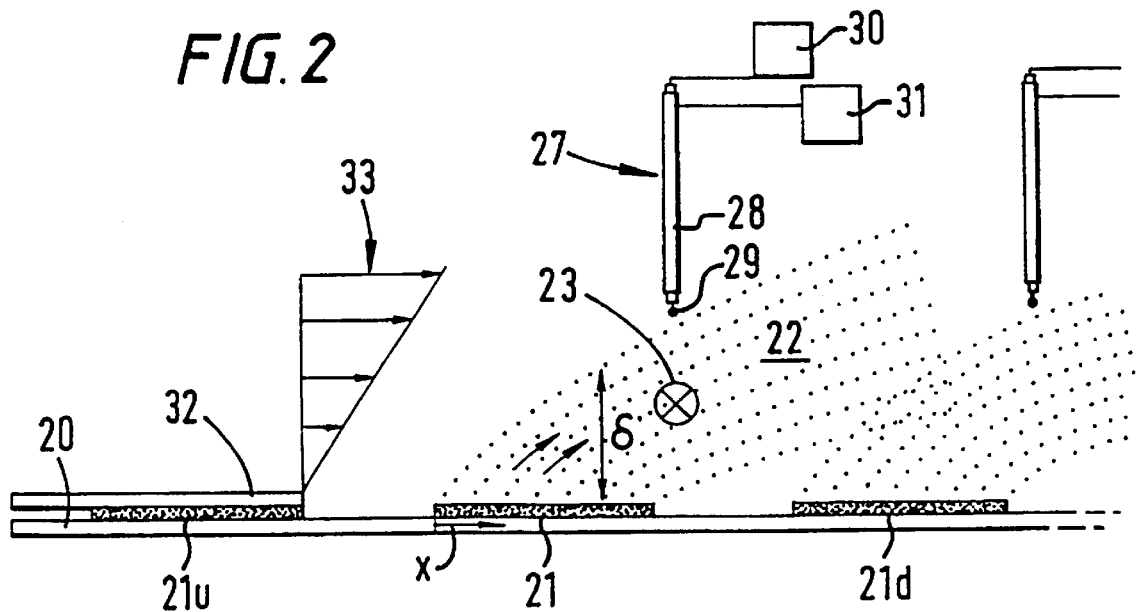
FIG. 2 is a schematic showing REMPI microelectrode detection of products formed by reactant contact of a catalyst library with physical masking.
Figure 3:
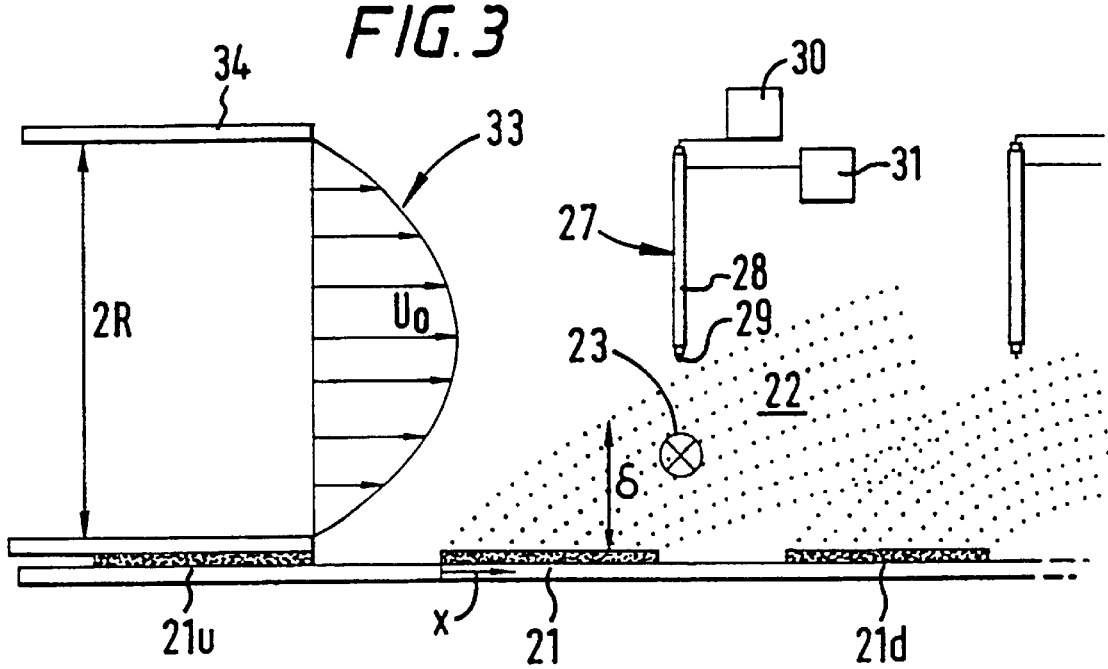
FIG. 3 is a schematic showing REMPJ microelectrode detection of products formed by reactant contact of a catalyst library through a dedicated reactant feed tube.
Figure 4:
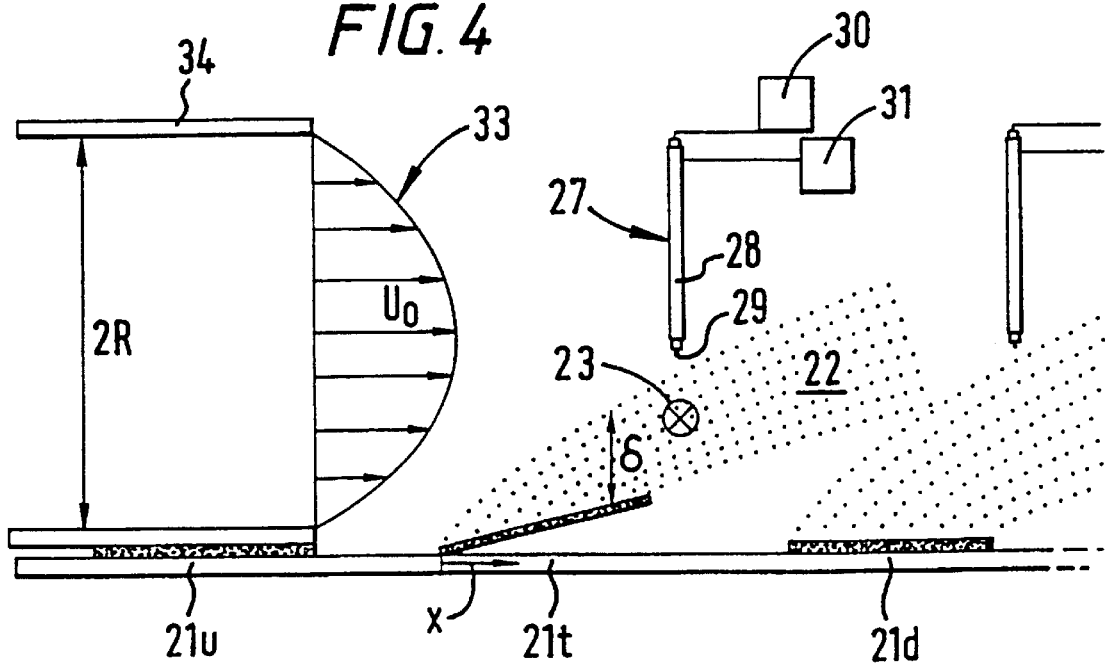
FIG. 4 is a schematic showing similar to FIG. 3 having a tilted test site.

For heterogeneous catalyst libraries, the solid state catalysts may be arranged in rows of catalyst clusters on a flat sheet to expedite the screening process. In addition, monolithic, or honeycomb, structures with well defined channels can also be used to generate suitable catalyst libraries. The catalyst sites can also be created to be porous or non-porous depending upon the catalyst and method of preparation. FIG. 2 illustrates a non-porous, flat sheet catalyst library with reactant contact with the catalyst achieved by flowing reactant gases over the library followed by row screening of product plumes. The same numerals have the same meaning throughout this disclosure and in the figures. Test catalyst site 21 with upstream catalyst site 21$u$ and downstream catalyst site 21$d$ are shown on substrate 20 with mask 32 shielding upstream catalyst site 21$u$ from the reactant gas stream indicated by reactant velocity profile 33. The gases containing products must be removed from the library after their emanation from the sites to minimize product circulation in the reactor. In the arrangement shown in FIG. 2, the catalyst sites upstream from the test catalyst site, 21, must be masked to prevent signal crossover from different sites. If the upstream sites are not masked and if some of these sites are catalytic, products formed at these sites would be transported downstream and interfere with the row screening process. Masking can be accomplished by using a physical mask to cover upstream catalysts sites, as shown in FIG. 2, or by introducing reactant gases directly onto the catalyst sites using dedicated gas reactant feed tubes, shown as 34 in FIG. 3. FIG. 4 shows tilted catalyst test site 21$t$ to promote transport of products away from the catalyst surface. This arrangement improves signal detection of products from the test site.

When reactant molecules pass over the test sites with catalytic properties, products will be formed at the surface. These products will then diffuse into the flowing gas stream and establish a product concentration boundary layer, or product plume 22, as shown in FIGS. 24. Assuming a constant catalyst surface concentration for the product, the product concentration layer thickness $\delta_c(x)=3.3(D \times L/U_o)^{1/3}$, where x is the distance from the leading edge of the catalyst site as shown in FIGS. 2–4, D is the molecular diffusion coefficient of the product, $U_o$ is a characteristic gas velocity as shown in FIGS. 3–4 and L is a characteristic dimension in the vertical direction, such as the height of the reactor or the diameter of the reactant feed tube shown in FIGS. 3–4 as 2R.

To illustrate some of the design issues involved, consider the solid state library of catalyst sites 5 mm long by 5 mm wide. Assuming a gas feed line diameter of 0.5 cm and a mean reactant gas velocity of 1.0 cm/sec and a diffusion coefficient of 0.1 cm²/sec which is typical for most gases at 1 atm, the concentration boundary layer thickness at 5 mm from the leading edge of the catalytic site can be estimated to be:

$$\delta(0.5)=3.3[(0.1)(0.5)(0.25)/1.0]^{1/3}=0.767 \text{ cm or } 7.67 \text{ mm}$$

This boundary layer is thick enough to pass a laser beam through and to photoionize products, if present. The diameter of the gas feed tube $2R$, the gas velocity $U_o$ and the catalyst site dimension x can be altered to further control the thickness of the concentration boundary layer. Additionally, test sites $21t$ can be tilted, as shown in FIG. 4, during the screening process to promote the transport of products away from the catalyst surface.

Figure 5:
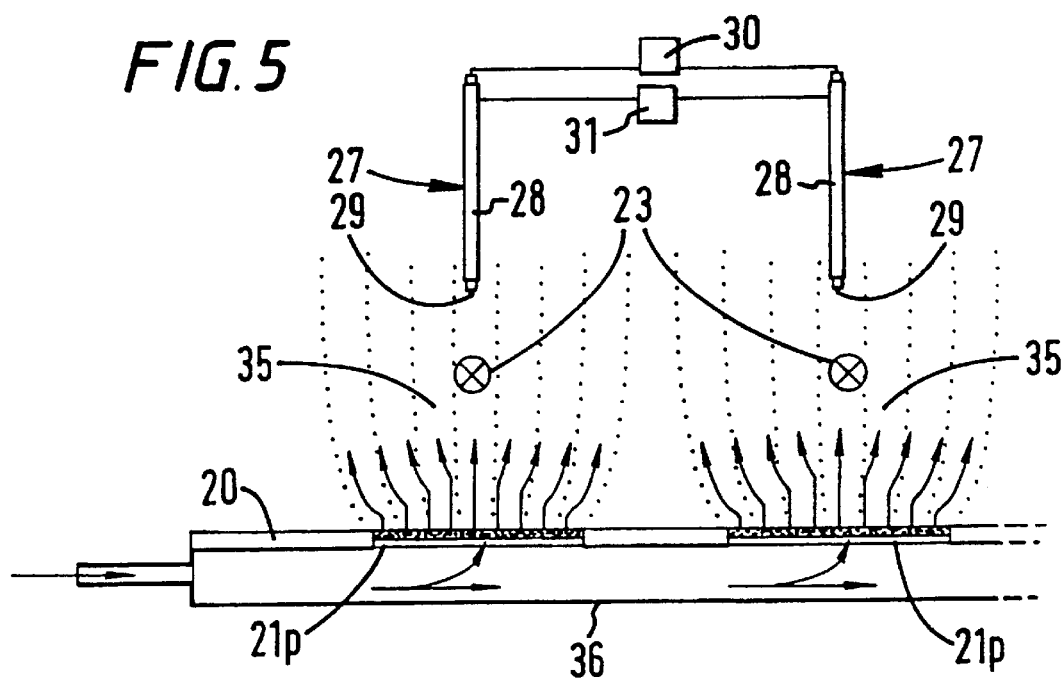
FIG. 5 is a schematic showing REMPI microelectrode detection of products formed by reactant contact of a catalyst library with flow through porous sites.

When porous catalyst libraries are generated, reactant gases can also be passed through the sites in the library generating a product plume above the test catalyst sites, as shown in FIG. 5. In this embodiment, the reactants pass through all of the catalyst sites thereby rendering simultaneous screening of all sites on the library feasible. As shown in FIG. 5, reactants are passed through reactant plenum 36 to and through porous test sites $21p$ forming product plumes 35 which are measured in the same manner as described above.

Figure 6:
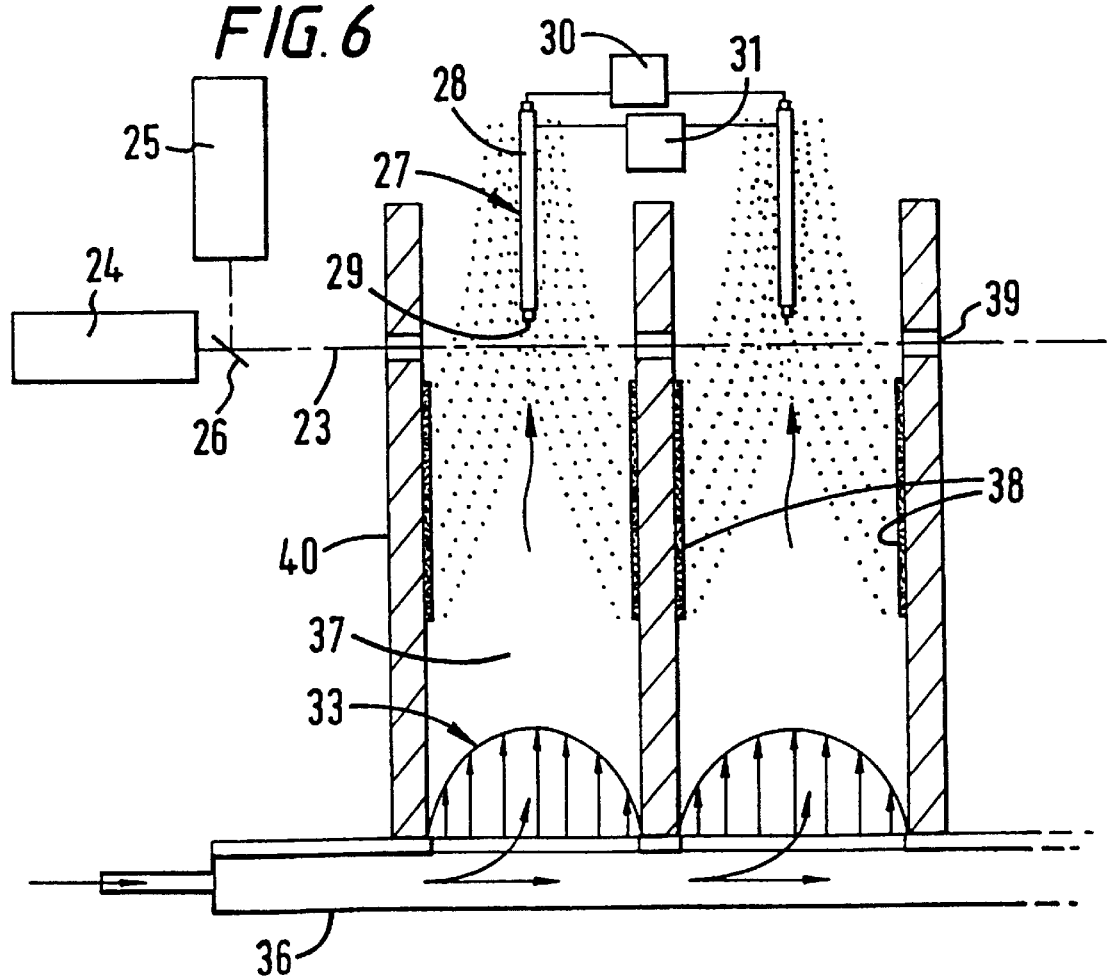
FIG. 6 is a schematic showing REMPI microelectrode detection of products formed by reactant contact of a catalyst library of catalyst coating on a monolithic structure.

Catalyst libraries may also be created, as shown in FIG. 6, using monolithic structures 40 wherein reactant gases will also pass through channels 37 over catalyst coatings 38 forming product gases which pass through laser beam 23 and over microelectrodes 27. In this embodiment, simultaneous screening of the entire library is readily accomplished. Microelectrodes 27 may be inserted into channels 37, as shown in FIG. 6, to significantly reduce signal crossover between catalytic sites. Optical access to the product gases in each channel must be provided through small windows 39 for the laser beam, as shown in FIG. 6. As a consequence of good spatial resolution and site separation provided, monolith structures provide a good framework for high throughput and simultaneous screening of high density catalytic libraries.

Figure 7:
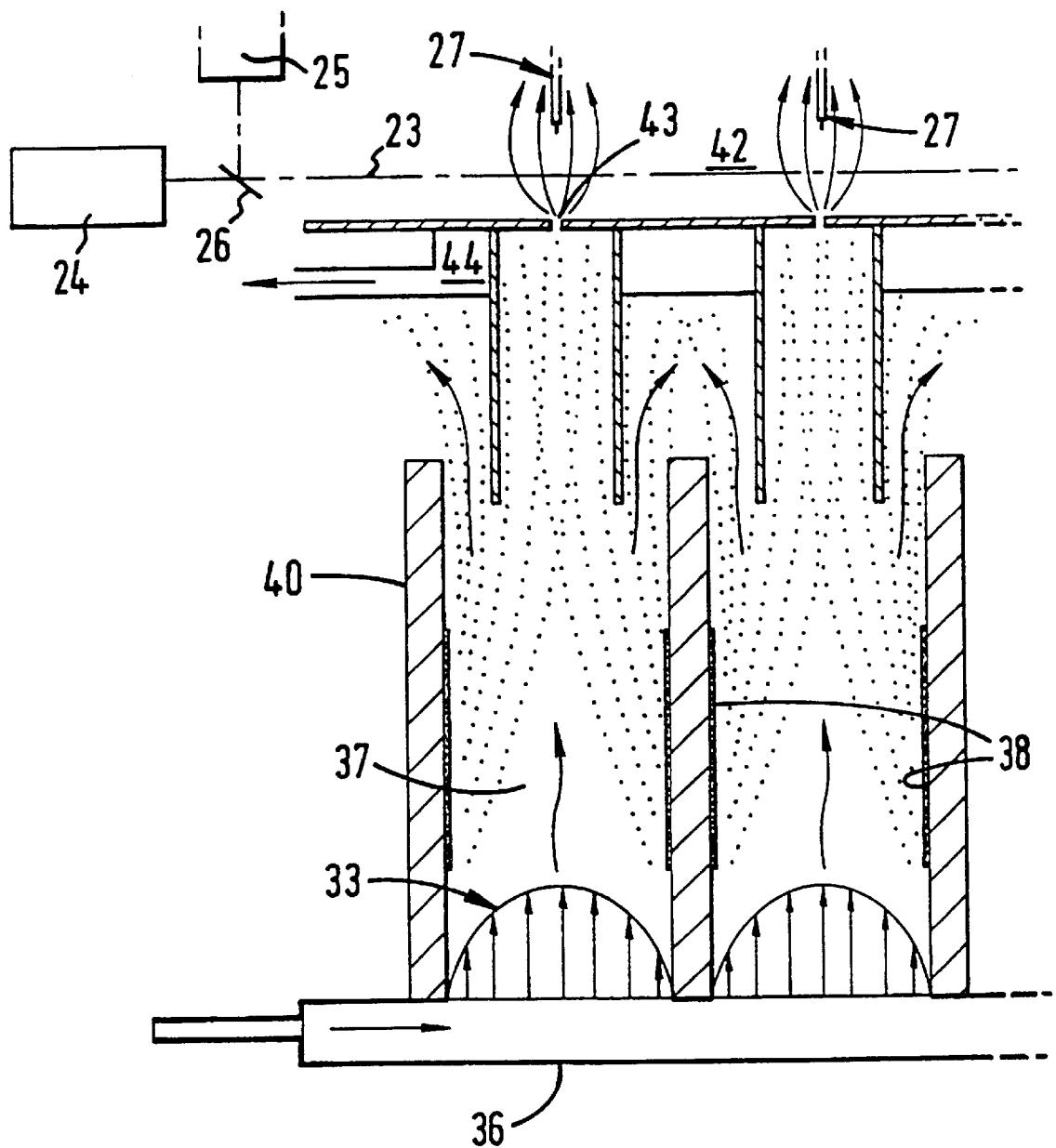
FIG. 7 is a schematic showing of a monolithic catalyst library with expansion cooling of products for REMPI microelectrode detection.

When the high temperature microelectrode REMPI spectra of the product molecules do not have distinguishing features or have features exhibiting overlap, products must be cooled to improve REMPI spectra. This can be readily accomplished, as shown in FIG. 7, by expanding a portion of the product gas plumes 41 emanating from the library sites 33 into vacuum chamber 42 through small orifices 43. Portions of the product gas directed through orifices 43 undergo adiabatic expansions forming supersonic jets in vacuum chamber 42 thereby decreasing the gas temperature resulting in significant simplification of the REMPI spectra. In addition, as shown in FIG. 7, precooling thermal exchanger may be located upstream of orifices 43 to reduce the temperature of the product gases prior to passage through orifices 43. Gas flow into a vacuum chamber can also be pulsed to improve the pumping requirements. For an ideal gas with a heat capacity ratio $\gamma$, that is $\gamma=c_p/c_v$, the temperature of the gas is related to pressure by the following relationship under adiabatic conditions: $T_2=T_1(P_1/P_2)^{(1-\gamma)/\gamma}$ wherein $T_1$, $P_1$ and $T_2$, $P_2$ are the initial and final temperatures and pressures, respectively. For example, for $\gamma=1.4$ and an initial temperature of 800 K and 760 Torr pressure, the temperature of the adiabatically cooled gas expanded into a vacuum at $10^{-3}$ Torr will be:

$$T_2=800(10^{-3}/760)^{(1.4-1)/1.4}=16.7 \text{ K}$$

This temperature is suitable for generation of an excellent REMPI spectra. Castaldi, M. J. and Senkan, S. M., 1998, supra. Simultaneous product screening of the catalyst library can be achieved by photoionizing the products using laser beam(s) 23, followed by detection of photoelectrons or photoions using microelectrodes 27 placed inside vacuum chamber 42 in close proximity to the expanding jet.

Figure 8:
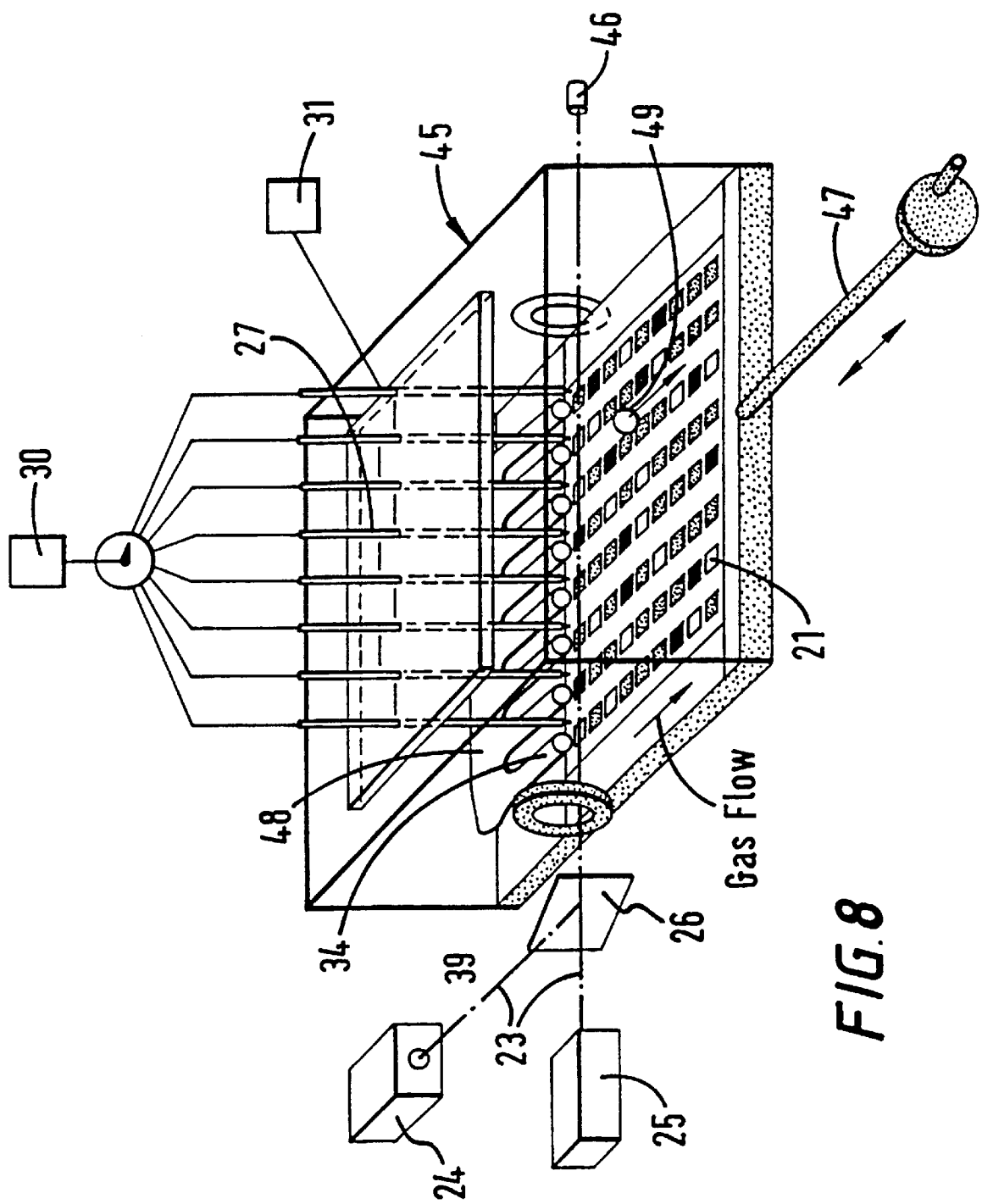
FIG. 8 is a schematic showing of a reactor with a flat plate solid catalyst library with row REMPI microelectrode detection.

FIG. 8 schematically shows a flat plate solid state catalyst library containing seventy two test sites 21, arranged 8 rows wide by 9 rows axially which are sufficiently separated from one another to result in minimal intersite diffusion of product gases, within reactor 45. Contact of reactants with the catalytic test sites is achieved by use of reactant feed tubes 34, as described with reference to FIG. 3, which effectively mask the upstream catalyst sites. Each of the test sites in a row being screened has a dedicated microelectrode 27 for product gas detection, eight as shown in FIG. 8, for screening by row. Arranging the test sites in rows expedites screening in a row-by-row fashion using a single laser beam and provides simultaneous screening of eight sites. Any row size can be accommodated using this invention. However, any library pattern having specific addresses for individual test sites can be screened by moving the library with a computer controlled two-dimensional translation device. The smallest site size, providing the highest library density, is determined by the gas phase dispersion rate of product gas between test sites. Consequently, different products can allow the generation and testing of different library densities. In the row screening process, as exemplified in FIG. 8, laser beams 23 pass through window 39 of reactor 45 and through the product gases above the test sites 21, perpendicular to the reactant gas flow from reactant feed tubes 34 and passes through the product gas plumes of all of the sites in a row, as indicated by the dotted line, and exits reactor 45 to laser beam dump 46. Reactant feed tubes 34 are supplied by reactor gas supply manifold 48. In FIG. 8, two lasers are indicated, however, any number of lasers may be used in a given application. Based upon the numerical design example given above, positioning of the laser beam about 5 mm above the substrate surface should be adequate for the laser beam to intercept the product plume and generate photoions, if a product is formed. Product gas exits reactor 45 through gas outlet 49. However, the laser beam may be placed anywhere in the product plume to maximize signal generation. It is apparent that if the test site is not catalytic, no product formation and therefore no photoionization will take place. Photoions and photoelectrons generated are collected by the microelectrodes 27 positioned in close position above the laser beam. Based upon the above numerical design example, microelectrodes can be positioned anywhere beyond 5 mm above the test site surface and in close to the laser beam to maximize signal intensity. However, microelectrodes can be placed at different positions above the test sites to maximize signal collection in conjunction with the local fluid dynamics of the product plume. As noted above, the library substrate can also serve as the ground or cathode, or a microelectrode can be placed through a nonconductive substrate, if necessary, or microelectrodes can include both the anode and cathode as shown in FIG. 8. The microelectrodes are powered from DC power source 30 through a multichannel switch and the measured signal of each microelectrode fed to detector 31. After testing of a particular row, the library can be moved either upstream or downstream, using library translator 47, to position the next row of sites for catalytic screening.

Figure 9:
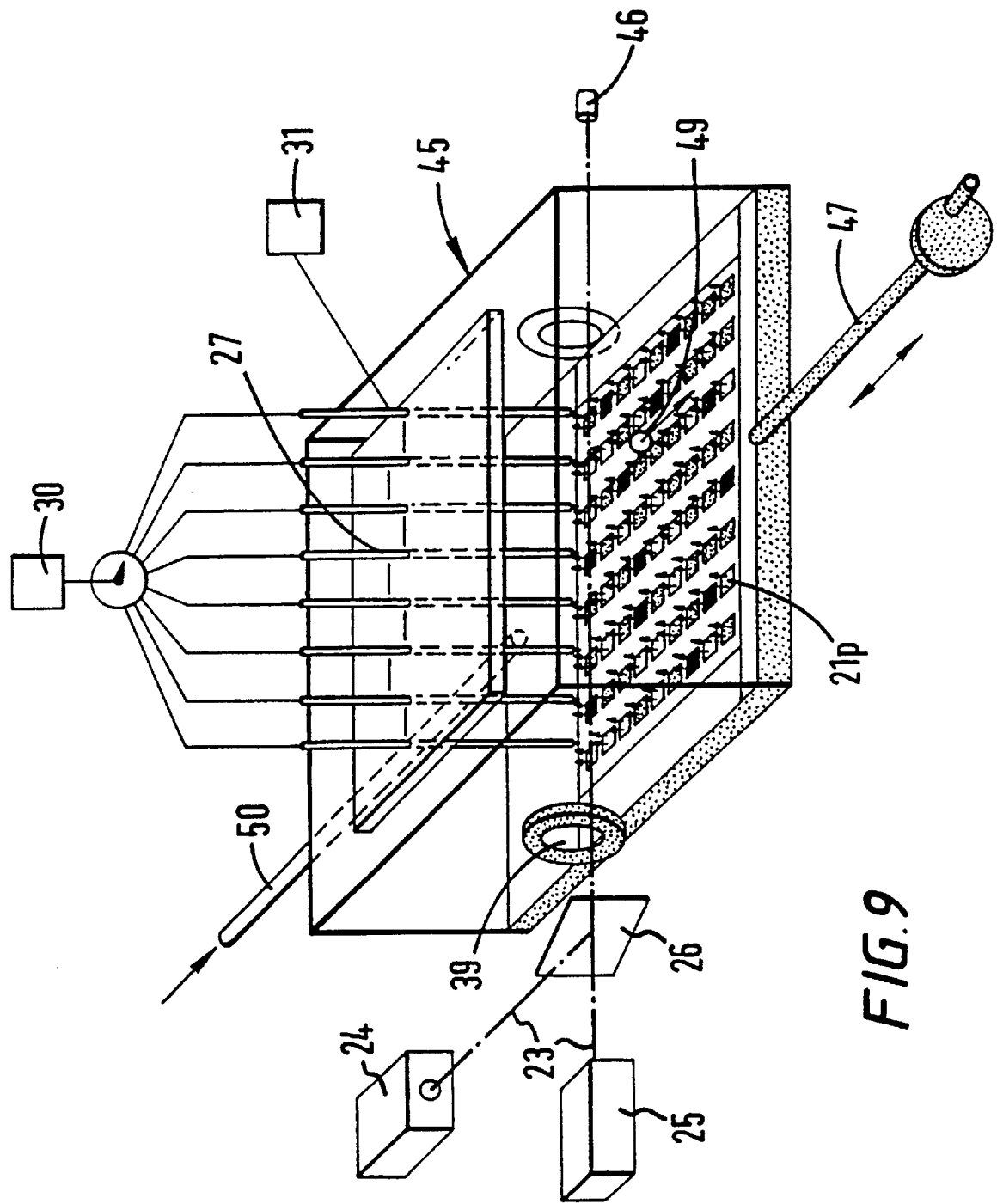
FIG. 9 is a schematic showing of a reactor with a flat plate catalyst library having reactant flow through porous sites and row REMPI microelectrode detection.
Figure 10:
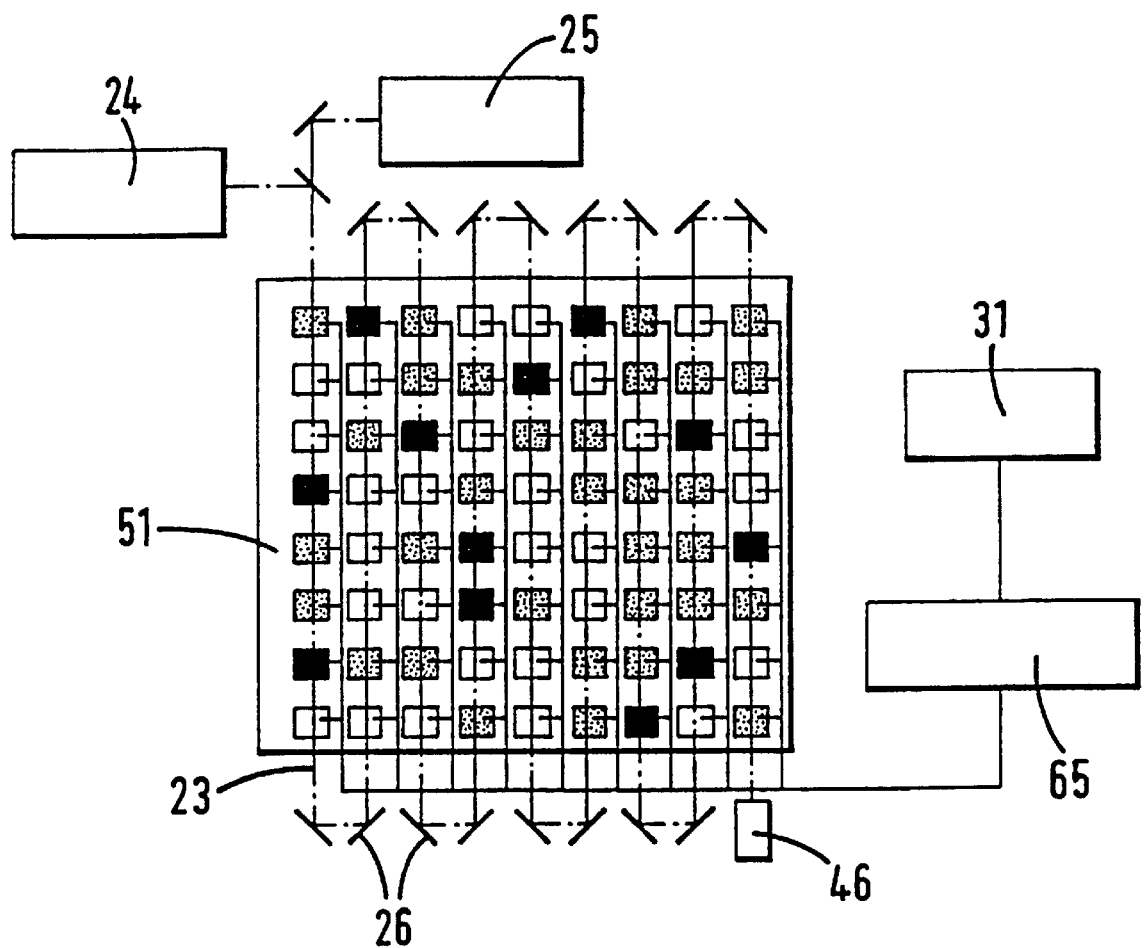
FIG. 10 is a schematic top view of a reactor as shown in FIG. 9 having simultaneous REMPI detection of all sites.

Another embodiment of this invention to exemplify the row screening process is shown in FIG. 9. The embodiment shown in FIG. 9 is similar to FIG. 8 except that porous catalyst libraries having porous test sites $21p$ are fed reactant gas from a plenum beneath them which is supplied reactant gas through reactant gas supply inlet 50. The reactant gas passes through porous test sites 21p forming a plume above each test site simultaneously as indicated by the arrows. The reactor can be rotated 180° around the x-axis, if desired, to enhance product detection by altering the natural convection processes in the reactor vessel. As shown in FIG. 9, screening is done on a row-by-row in similar manner as described with respect to FIG. 8. Alternatively, screening of all sites simultaneously may be done by equipping each site with a dedicated microelectrode and providing the ionizing laser beam 23 to pass all sites simultaneously using turning mirrors 26, as shown in the top view of FIG. 10. Optical fibers may also be used to direct the laser beam to all sites simultaneously. Signals from the microelectrodes are then detected and recorded by a dedicated detector for each site on catalyst library 51 or by use of a computerized multi-channel switching system 65 to rapidly and sequentially detect the signal coming from each site. It is apparent that any catalyst library size and shape can be accommodated and operated in this simultaneous screening mode as long as each site is individually addressable.

Figure 11:
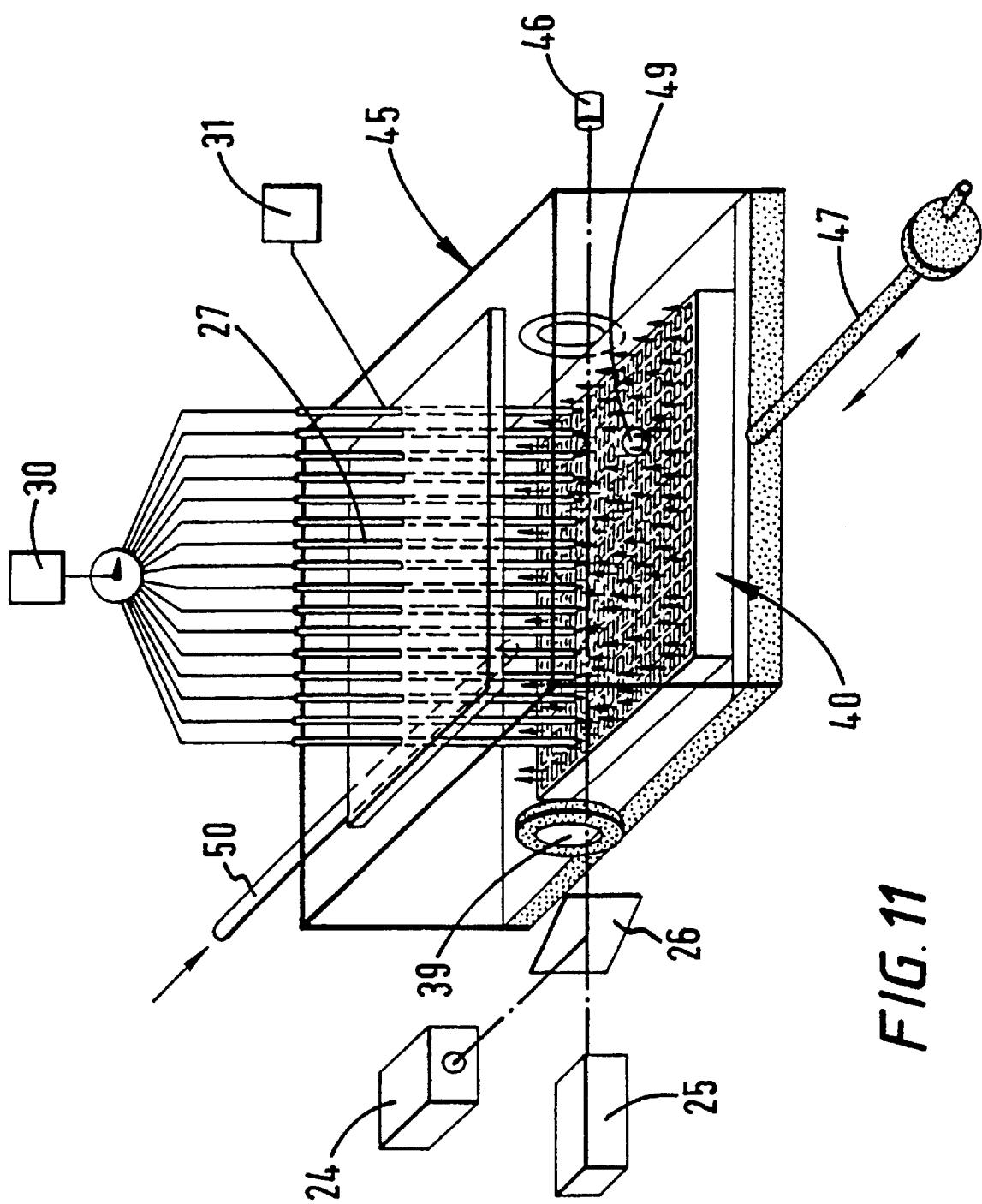
FIG. 11 is a schematic showing of a reactor with a monolith solid catalyst library having reactant flow through with row REMPI microelectrode detection.

Another embodiment of this invention is shown in FIG. 11 which schematically shows a 16 by 16 or 256 site monolith structure 40 as described with respect to FIG. 7 forming a solid state catalyst library. Any monolith cell density can be used. Reactant gases are provided through reactant gas supply inlet 50 to a manifold beneath the library and pass upwardly through the channels, passing over or through catalysts, generating product plumes which may be measured within the channels as shown in FIG. 6, above the exit from the channels as shown in FIG. 9, or following cooling by a supersonic jet into a vacuum chamber as shown in FIG. 7. Catalyst screening may be accomplished using row-by-row method as shown in FIG. 11 or by screening all sites simultaneously as described with respect to FIG. 10.

Figure 12:
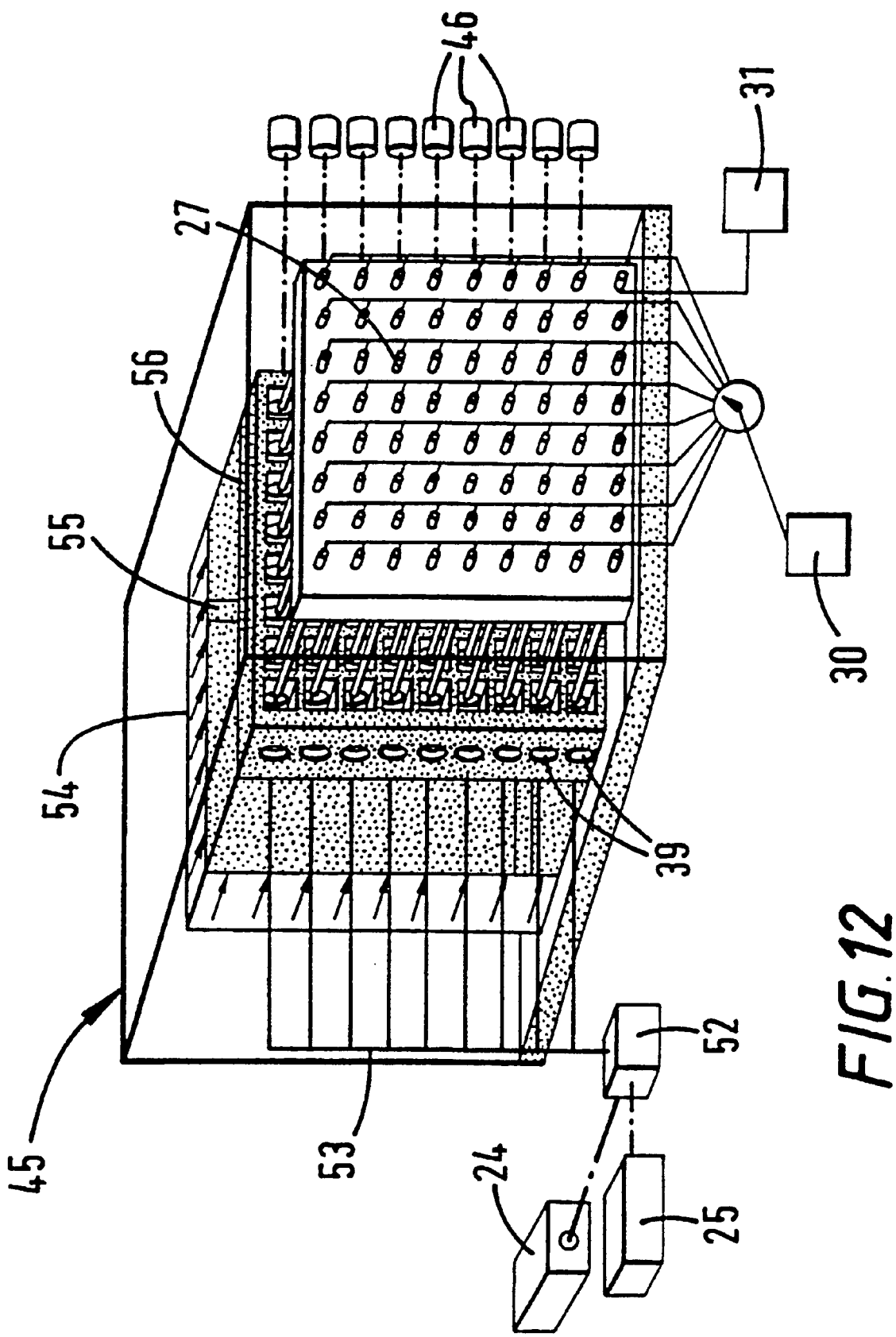
FIG. 12 is a schematic showing of a reactor with a monolith catalyst library having simultaneous REMPI detection of all sites.

Another embodiment of a monolith supported catalyst library screening structure within a reactor is shown in FIG. 12, generally using the arrangement as described with respect to FIG. 6. As shown in FIG. 12, a separate catalyst library monolith 55 having 72 sites and a separate catalyst screening monolith 56 forms the catalyst screening structure within reactor 45. A dedicated microelectrode 27 is provided inside of each monolith channel. Upstream of each microelectrode 27, optical access to each channel is provided by laser access windows 39. Reactant gases are introduced by reactant gas flow distributor and enter each of the individual library channels, as indicated by the arrows, to pass over the catalyst sites. Products are detected downstream inside the screening monolith 56. Lasers emanating from tuneable laser sources 24 and/or 25 are directed to each row of the screening monolith 56 via beam splitters 52 and through laser windows 39 to pass through each of the channels in the row through the internal laser windows as shown. This arrangement provides simultaneous screening of all sites in the library. Different laser beams can be directed to different rows in the screening monolith 56 to screen for different products. This technique can also be applied for screening other library configurations. Fiber optic lines 53 can also be used to direct the laser beam to the library sites. If product cooling is desirable, this can be accomplished by adiabatically expanding the product gas plumes into a vacuum chamber through small orifices, as shown in FIG. 7.

In the above description of catalyst screening apparatus and techniques the temperature has been the same at all catalyst sites, which would be appropriate for screening for new catalysts or to modify catalysts. It is possible, according to this invention, to construct catalyst libraries having individually temperature controlled sites wherein different sites would be maintained at different temperatures or their temperatures could be programmed to follow a specified temperature-time program. Such differing temperatures generates information on the effects of reaction temperatures on catalyst activity and selectivity. Using micromachining, individually temperature controlled and programmable sites may be economically constructed, such as done for thermal inkjet printer heads. It is readily apparent that the amount of insulation provided by the substrate and the temperature programming demands influence the intersite spacing and the density of the catalyst libraries with temperature controlled sites.

It is also possible to screen an entire catalyst library using a batch mode operation. In the batch mode, the entire catalyst library is first isolated from the reactant gases by a physical mask. The test chamber is then purged and filled with fresh reactant gases. The chamber contents are allowed to reach thermal equilibrium which can be monitored by thermocouples placed within the test chamber. The physical mask is then removed exposing either a specified section or the entire catalyst library to reactant gases. Since there is no forced convection, diffusion and natural convection are the major modes of gas transport in the test chamber. The sites that are catalytic then generate reaction products which diffuse into the bulk gas phase generating a product concentration plume. For a constant concentration of the product, the concentration penetration depth, $\delta_c(t)$, can be approximated by the relation:

$\delta_c(t)=(12Dt)^{1/2}$ where D is the diffusivity and t is the time.

The concentration penetration depth must be kept less than the intersite spacing to prevent overlapping of concentration plumes from adjacent sites resulting in signal crossover. For a flat plate catalyst library, assuming 1 cm intersite spacing, $\delta_c=1$ and 0.1 cm$^2$/sec for gas diffusivity, the REMPI measurements for the entire library must be completed in about 1 second to avoid overlap of concentration boundary layers. Available fast electronic equipment can meet these requirements. Larger site dimensions and/or placing physical barriers between sites can significantly decrease intersite diffusion-mixing rates, thereby providing longer times for measurements. In the case of monolith structures, physical walls existing between the sites substantially decrease intersite diffusion, thereby allowing acquisition of data for longer periods of time by microelectrodes placed near or inside the channels for detection of photoions and/or photoelectrons created by the laser beam. An advantage of the batch system is that it can be used to simultaneously screen all sites in the solid state catalyst library.

Figure 13:
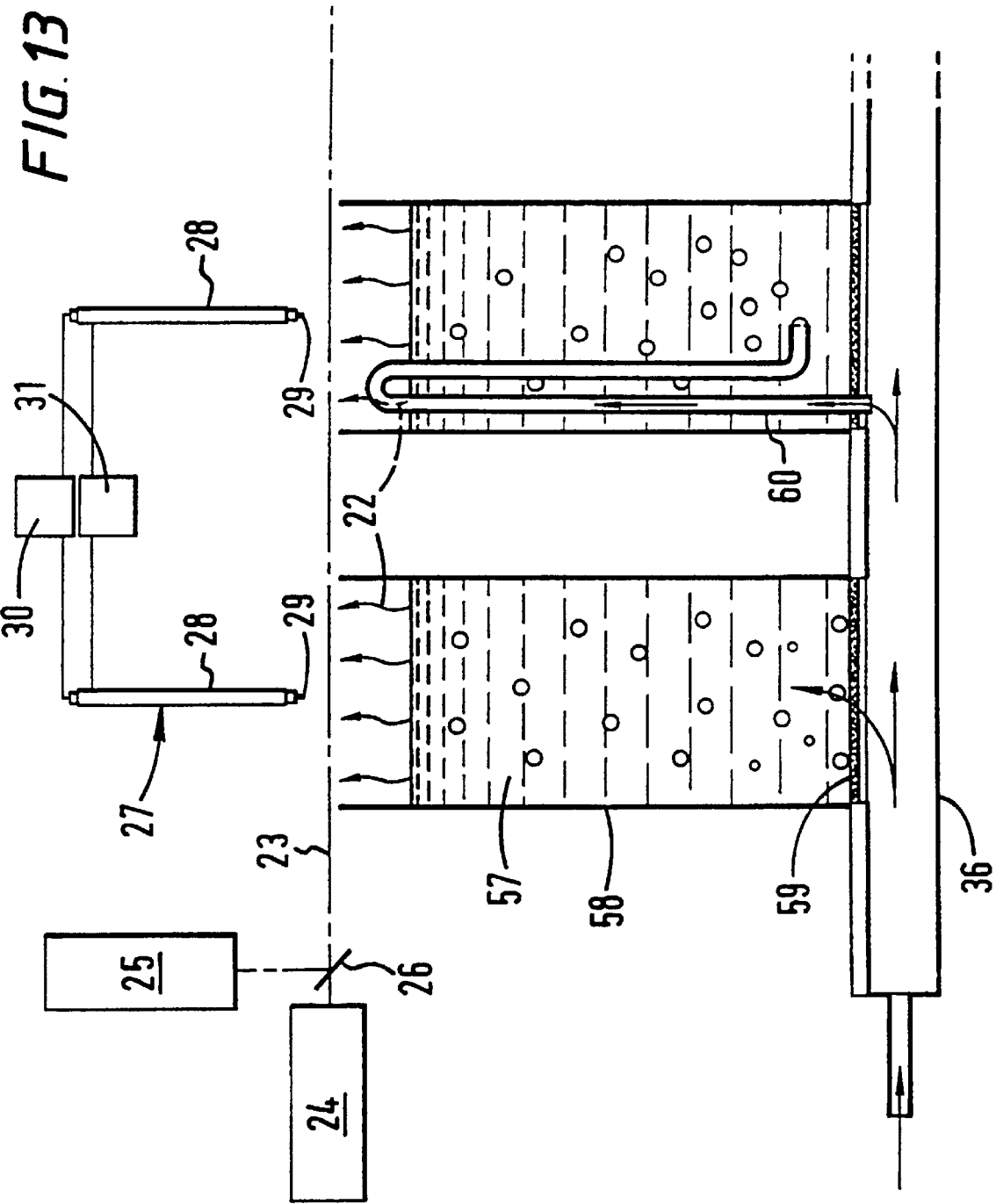
FIG. 13 is a schematic showing of a catalyst library with reactant contact for homogeneous catalyst sites with REMPI microelectrode detection of products.

One embodiment of a homogeneous catalyst library which can be synthesized, as described earlier, and screened according to this invention is shown in FIG. 13 wherein catalyst solution 57 is maintained in container 58 and reactant gases are bubbled through the liquid. Gas dispersion through the liquid catalyst can be achieved in any suitable fashion as will be apparent to one skilled in the art, for example, pressurised reactant gases can be fed through reactant plenum 36 and forced through a controlled porosity distribution plate at the bottom of the sample site, as shown on the left in FIG. 13. Alternatively, reactant gases from reactant plenum 36 may be bubbled through a capillary sparger 60 at each sample site, as shown on the right in FIG. 13. Gaseous products 22 formed leave the liquid catalyst solution, as indicated by the arrows in FIG. 13, and product gas detection performed in any of the manners described earlier. The minimum diameter of container 58, which controls the library density, must be established from considerations of the surface tension and viscosity of catalyst solution 57 which influence the extent of gas dispersion and liquid carryover.

Figure 14:
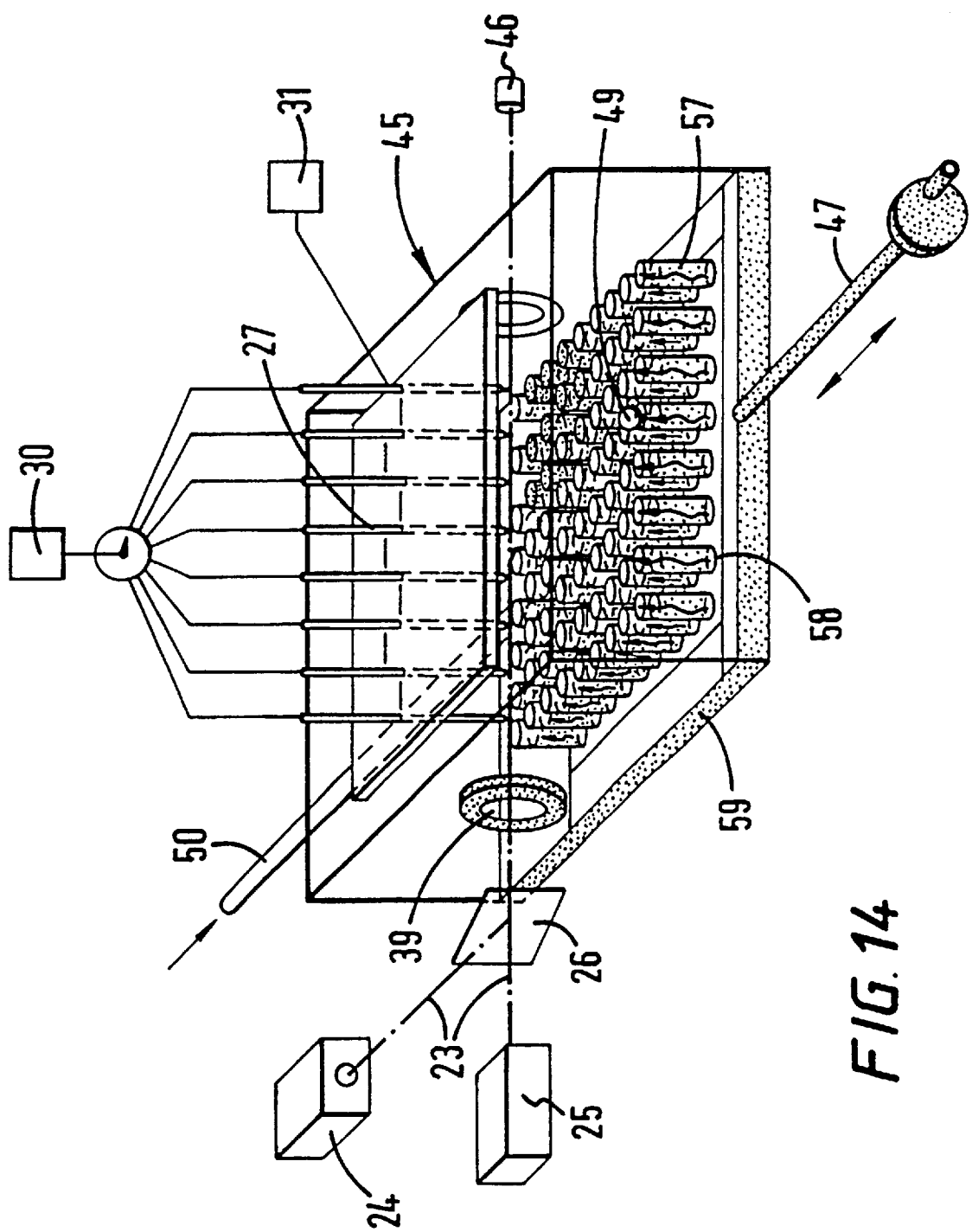
FIG. 14 is a schematic showing of a reactor with a homogeneous catalyst library with reactant flow through with row REMPI microelectrode detection of products.

FIG. 14 is a schematic showing of catalyst library screening using a homogeneous liquid catalyst library, as described with respect to FIG. 13, within reactor 45. REMPI catalyst screening can be either on a row by row basis, as illustrated in FIG. 14, or the entire catalyst library can be screened simultaneously, using the method as described with respect to FIG. 10. The reactor system exemplified in FIG. 14 may also be used to screen solid catalyst powders which can be placed in the container, as will be described in further detail with respect to FIG. 15.

Figure 15:
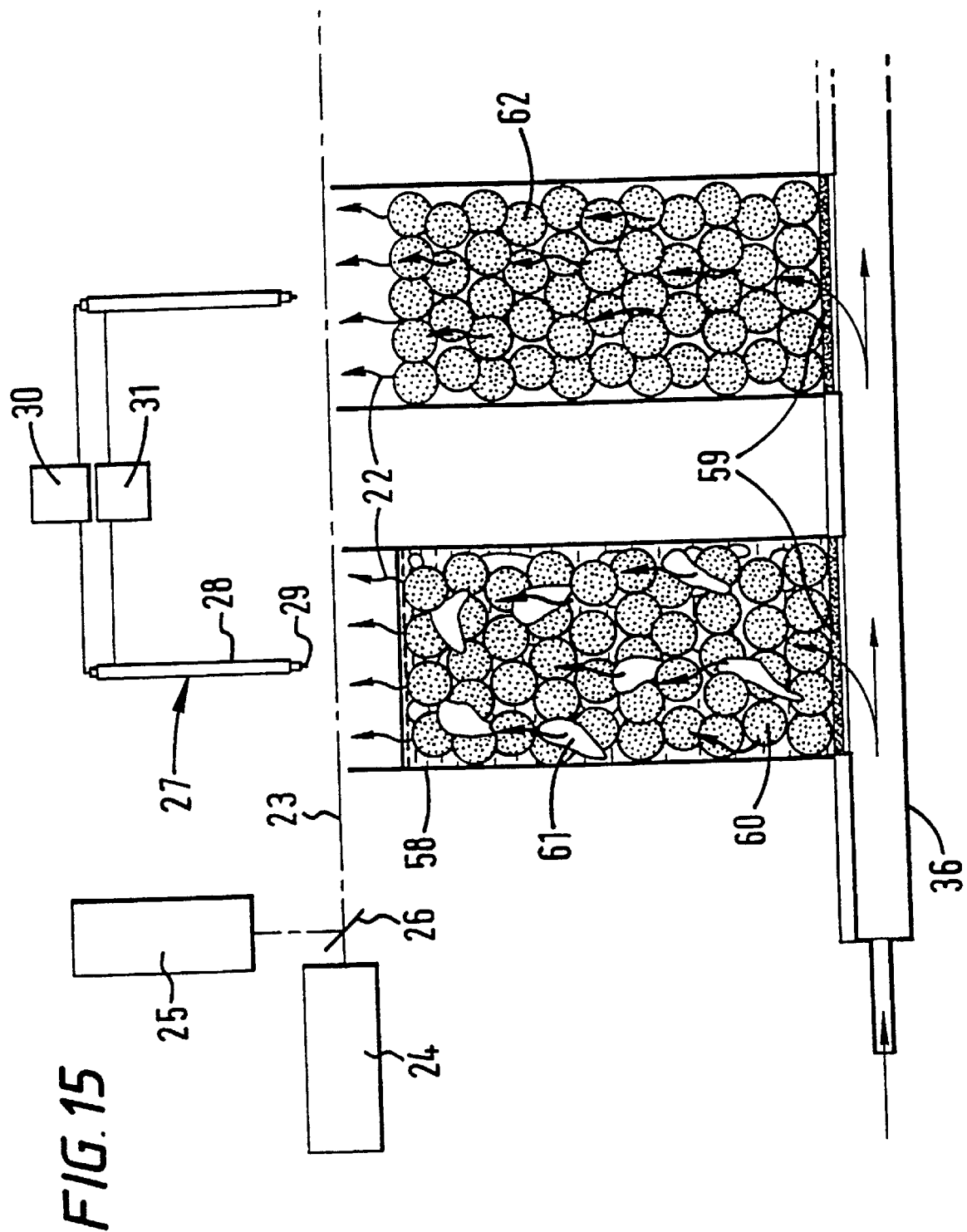
FIG. 15 is a schematic showing of a catalyst library using solid catalyst particles for gas distribution and for catalyst contact with REMPI microelectrode detection of products.

Solid particles may be incorporated into the liquid catalyst library to achieve three phase, gas-liquid-solid, operating conditions. The introduction of solid particles 60 to the liquid in container 58 enhances gas dispersion, forms smaller gas bubbles 61 to provide better gas-liquid contact and improves reactant conversion, thereby increasing the speed of library screening, is shown in the left hand portion of FIG. 15. The bed can also be fluidized, partially or fully, under the screening conditions. Product gases 22, indicated by arrows, emanate from container 58 and may be analyzed by any of the REMPI methods previously described. The solid particles used may be catalytic, thereby providing the opportunity of screening multi-phase catalytic reactions. Homogeneous liquid catalysts may also be placed into porous particles, for example to immobilize proteins or molten salt catalysts, in the systems as shown in FIG. 15. Solid catalytic particles 62 may be introduced into container 58, without liquid, to achieve gas-solid operating conditions, as shown in the right hand portion of FIG. 15. Catalyst powders, prepared in a number of different manners, can be placed within the container shown in FIG. 15 to create a micro packed bed reactor library. Reactant gases may be introduced to the packed bed reactors through plenum 36 and products formed detected using the REMPI microelectrode systems previously described.

Figure 16:
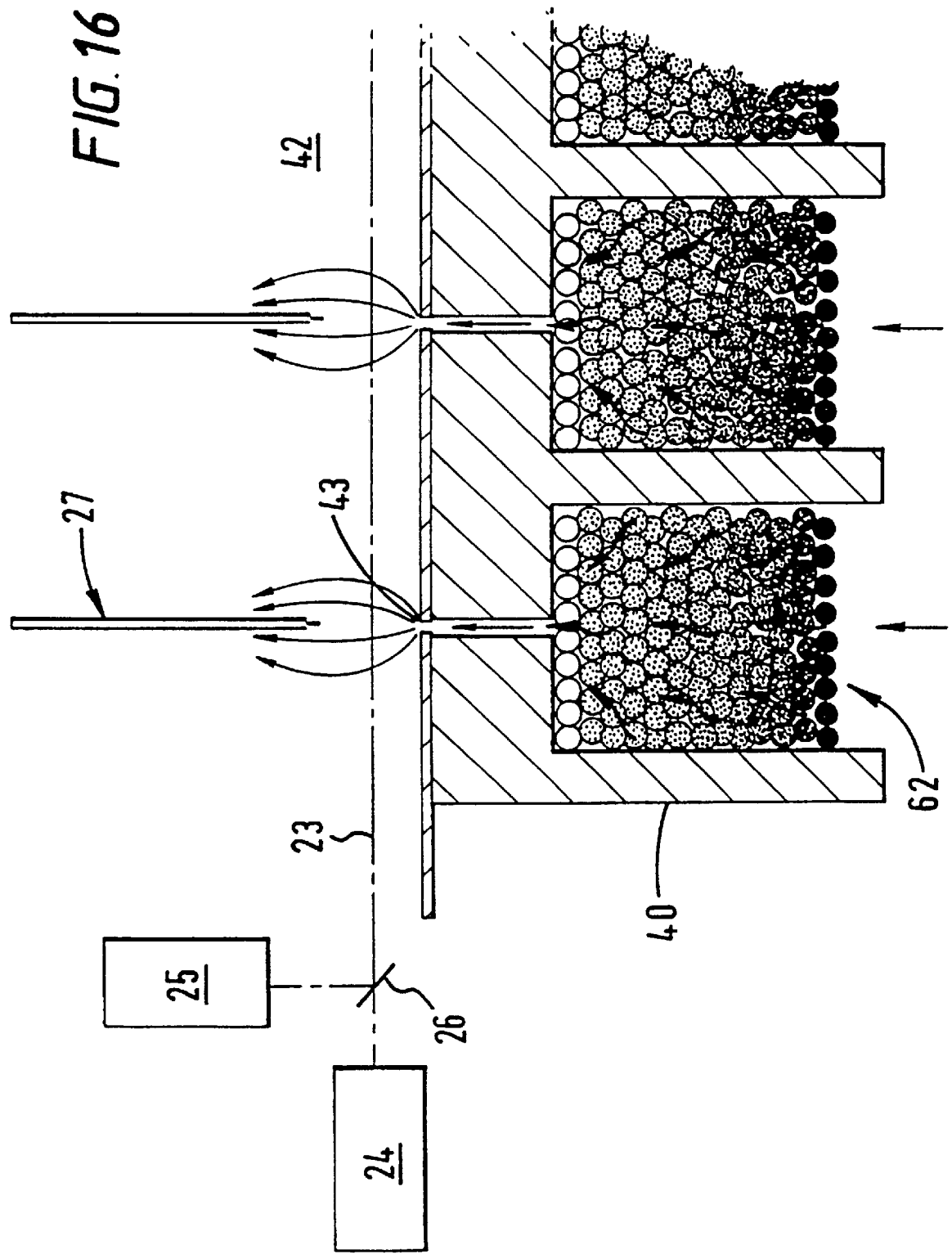
FIG. 16 is a schematic showing of a heterogeneous catalyst library with reactant flow through with expansion cooling of products for REMPI microelectrode detection.

FIG. 16 is a schematic showing of another catalyst screening method using catalyst particles in a monolithic library. Catalyst particles or powders 62, prepared in a number of different ways, can be placed into the cells of monolithic structure 40. The reactant gases are then passed through the packed bed of catalyst particles 62 and are discharged through a small channel/orifice 43 into vacuum chamber 42. The product jets then undergo expansion cooling and are subjected to laser beam 23 for the generation of photoions and photoelectrons. The photoions or photoelectrons generated are then detected by microelectrodes 27, as described above.

The magnitude of the REMPI signals produced by the photoionization of product species will be proportional to their concentration. In addition, the generated signals are also influenced by the operational parameters, such as, the power of the UV laser used, the DC bias voltage applied to collect the photoions/photoelectrons, the separation distance of the anode and cathode and the position of the microelectrode relative to the laser beam. Once optimized for the particular system to be used for catalyst library screening, the operational variables can be fixed so that the measured REMPI signals can be directly attributed to produce concentrations generated by the catalyst sites. Consequently, in addition to the qualitative, active versus inactive, screening of catalyst libraries, the REMPI microelectrode technique of this invention can be used to quantitatively rank the activities and selectivities of catalysts. Catalytically more active sites will produce higher concentration of products in the product plume and thereby generate larger REMPI signals, and likewise, less active catalyst sites will generate lower concentrations of products and thereby lower REMPI signals. In catalyst library quantitative screening, gas mixtures containing known concentrations of product gases are first passed sequentially over the library under conditions at which no reactions take place and the microelectrode responses noted. Using microelectrode responses to known product concentrations, calibration of each site and microelectrode may be achieved. These calibration functions are then used to determine the quantitative concentrations of products formed during the active catalyst screening process. If the catalyst loading is different at different library sites, this also must be accounted for in ranking of the catalytic activity of the sites. Alternatively, internal standards can be added to the reactant feed stream during the screening process to expedite the quantification of the activities and selectivities of catalyst sites.

The catalyst screening techniques disclosed can be utilized to obtain a greater spectrum of objectives. Two or more laser beam energies can be used sequentially to monitor two or more reaction products in a product plume, which is important to establish catalyst selectivity and to discover multifunctional catalysts. For example, the development of catalysts which not only maximizes the formation of specific products but also minimizes the formation of by-products or pollutants is an increasingly important objective in environmentally conscious manufacturing. In the practice of this invention, a series of laser pulses, each pulse specifically photoionizing a selected molecule, can be used to sequentially monitor different products. Since laser photoionization and product detection are fast processes, having time scales in microseconds, rapid screening of large potential catalyst libraries for multifunctional catalytic activity can be accomplished even with the sequential detection of a large number of species.

Figure 17:
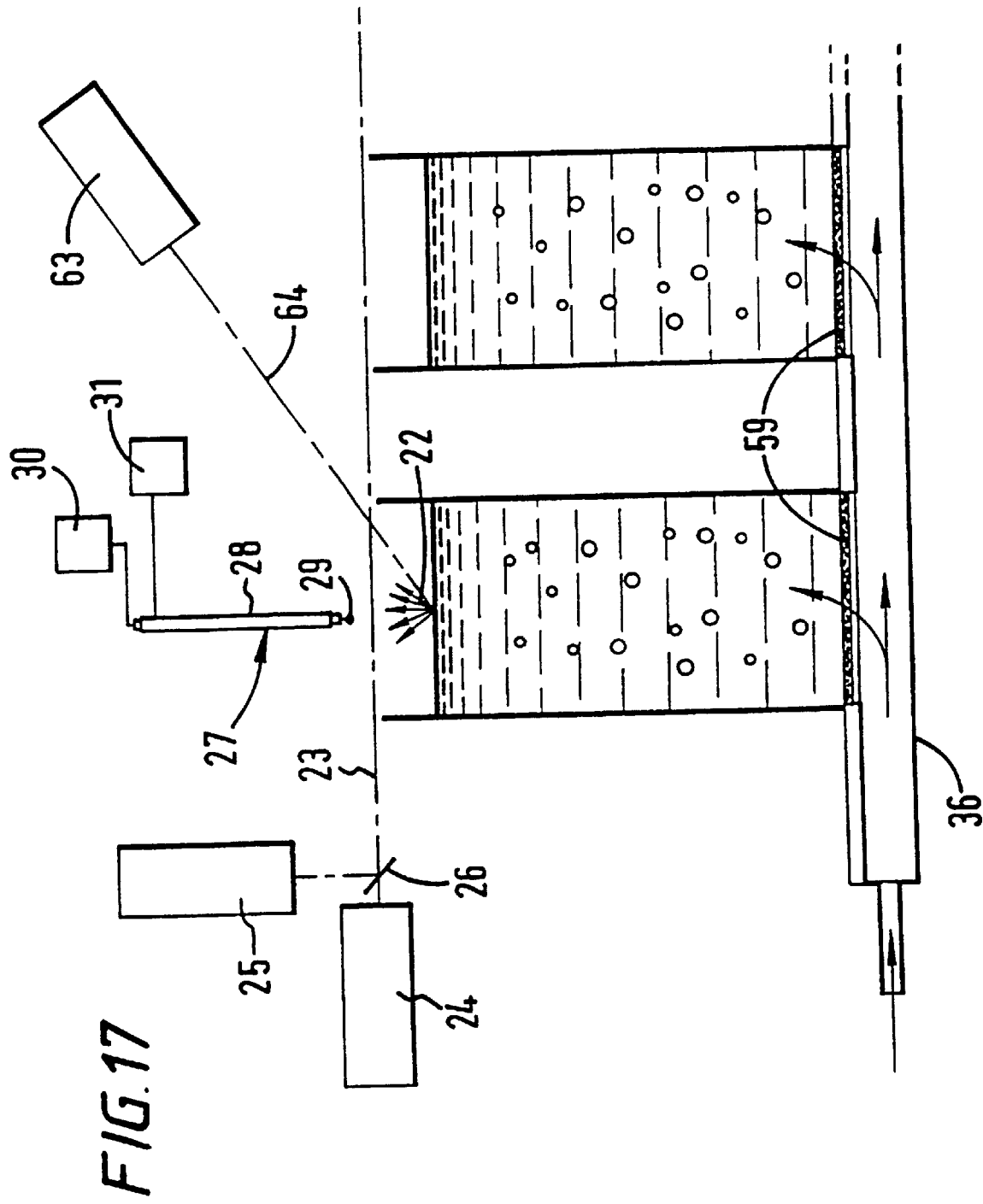
FIG. 17 is a schematic showing of a catalyst library using an ablation laser for gasification of solid and/or liquid products for REMPI microelectrode detection of products.

In some applications, the products formed by the catalytic reaction may be in the liquid or solid state, for example, reactions of high molecular biomolecules catalysed by enzymes, thus the direct application of REMPI is not suitable to screen catalytic activity and selectivity. The REMPI method, however, can be applied if the reaction products are first gasified. This can be accomplished by using a pulsed ablation laser, such as a pulsed $CO_2$ or excimer laser, to rapidly gasify product molecules from a liquid or solid surface. One embodiment using an ablation laser is shown in FIG. 17 wherein ablation laser source 63 generates ablation laser beam 64 to rapidly gasify product molecules from the surface of liquid catalyst solution 57 into gaseous product plume 22 which may be intercepted by ionization laser beam 23 and produced photoions and photoelectrons detected by any of the microelectrode methods described above.

It is evident from the above disclosure, that it is also possible to monitor reaction intermediates as well as reaction products using the REMPI microelectrode methods of this invention. The ability to monitor reaction intermediates, as well as products, greatly enhances the range of applicability of the methods of this invention. In addition, because measurements according to this invention can be undertaken in real time without any delay, fast transient processes can be monitored. This capability then leads to better understanding of the catalyst function and thus aids in the development of new and improved catalysts.

The following specific example is set forth in detail to specifically demonstrate this invention and should not be taken to limit the invention in any way.

The catalyst screening method of this invention was used in the catalytic dehydrogenation of cyclohexane into benzene according to the reaction $C_6H_{12} \rightarrow C_6H_6+3H_2$. This is a well established reaction which is catalyzed by transition and precious metals in the temperature range of 250° to 350° C. Rebhan, D. M. and Haensel, V., "A Kinetic and Mechanistic Study of Cyclohexane Disproportionation: An Example of Irreversible Hydrogen Transfer", J. Catalysis, 111, 397, 1988.

Supported Pt and Pd catalysts, 0.5% and 1.0% Pt and Pd on activated carbon, were obtained from Precious Metals Corp. These catalysts, as well as several inert carrier materials, silica and alumina, were then incorporated into one row in a library substrate in 5 mm by 5 mm cells similar to FIG. 5. The addresses for the catalysts and inert carrier materials were:

| Site No. | 1 | 2 | 3 | 4 | 5 | 6 | 7 | 8 |
|---|---|---|---|---|---|---|---|---|
| Material | Inert | 0.5% Pt | Inert | 1.0% Pd | Inert | Inert | 1.0% Pt | 0.5% Pd |

The catalyst library was then placed into a reactor and heated to 300° C. in the presence of an argon gas flow. Following establishment of the steady state operating temperature, which was determined by thermocouples inside the reactor, a cyclohexane reactant stream was introduced. The reactant stream composition was 13% cyclohexane in argon gas which was prepared by bubbling argon gas through cyclohexane liquid at about 25° C. by using a sparger.

Figure 18:
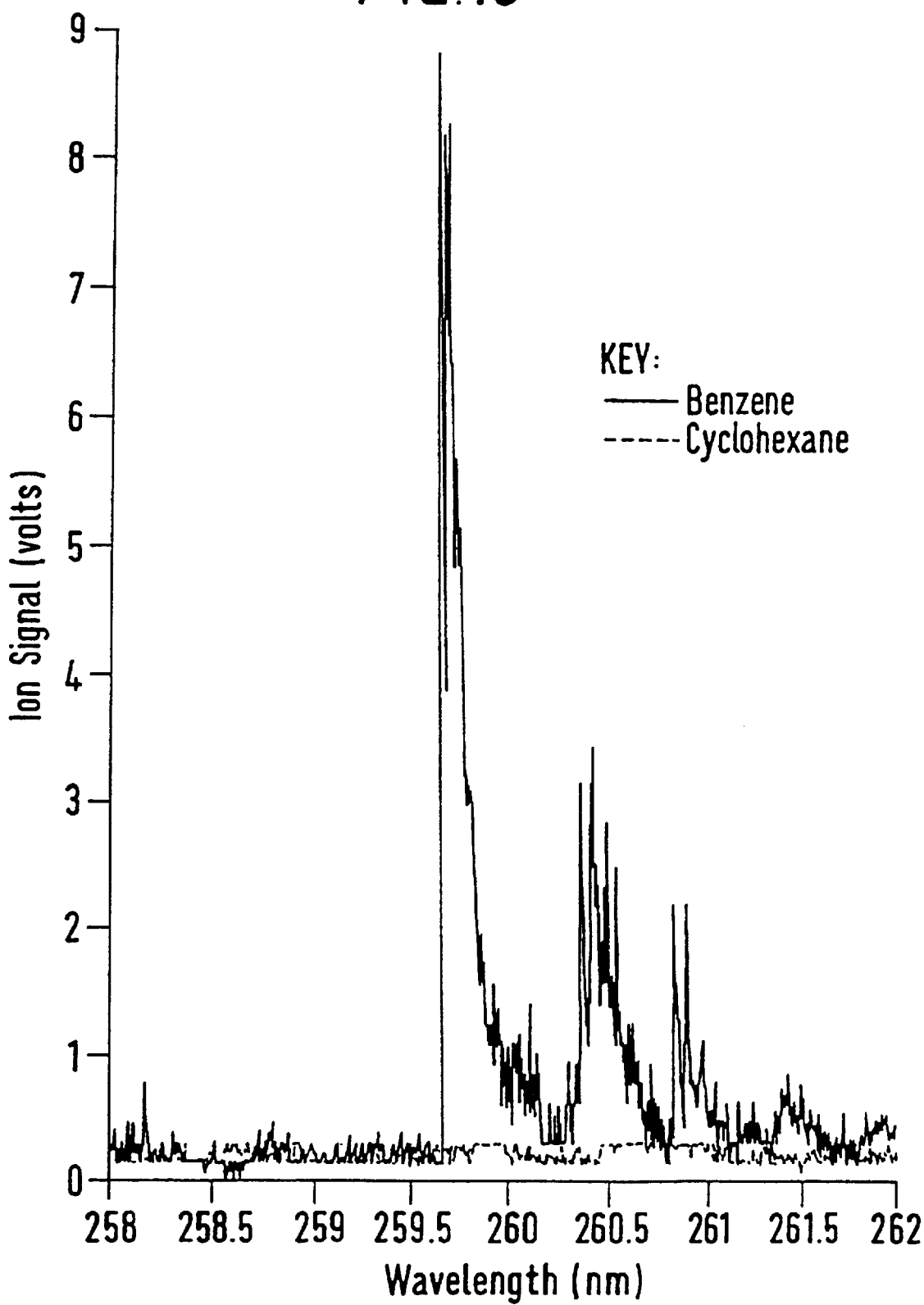
FIG. 18 is a molecular beam REMPI spectra for benzene and cyclohexane by TOF-MS.

The library screening process demands the unambiguous detection of benzene in a cyclohexane, hydrogen and argon mix. A suitable UV laser wave length for selectively producing benzene REMPI ions was identified in separate tests using a laser photoionization time of flight mass spectrometer, TOF-MS. Gas pulses of cyclohexane and benzene, each at a concentration of about 500 ppm in argon, were expanded into the vacuum chamber of the TOF-MS using a pulsed valve and the resulting jet/molecular beam was crossed by a pulsed UV laser beam in the 258–262 nm range to generate their photoionization and mass spectra. The UV laser had about 100 µJ/pulse energy and was obtained from the dye laser using Coumarin 500 dye. These measurements led to the conclusion that the REMPI ions produced by the 258–262 nm UV laser were exclusively due to photoionization of benzene, mass 78, with no photoions detected at masses 84 for cyclohexane or 40 for argon or 2 for hydrogen. No peaks other than the benzene parent at mass 78 were detected. FIG. 18 shows the REMPI spectrum of benzene and cyclohexane as determined by the TOF-MS technique. It is evident from FIG. 18 that benzene exhibits a major REMPI peak starting at 259.7 nm, where there is no contribution from cyclohexane.

Figure 19:
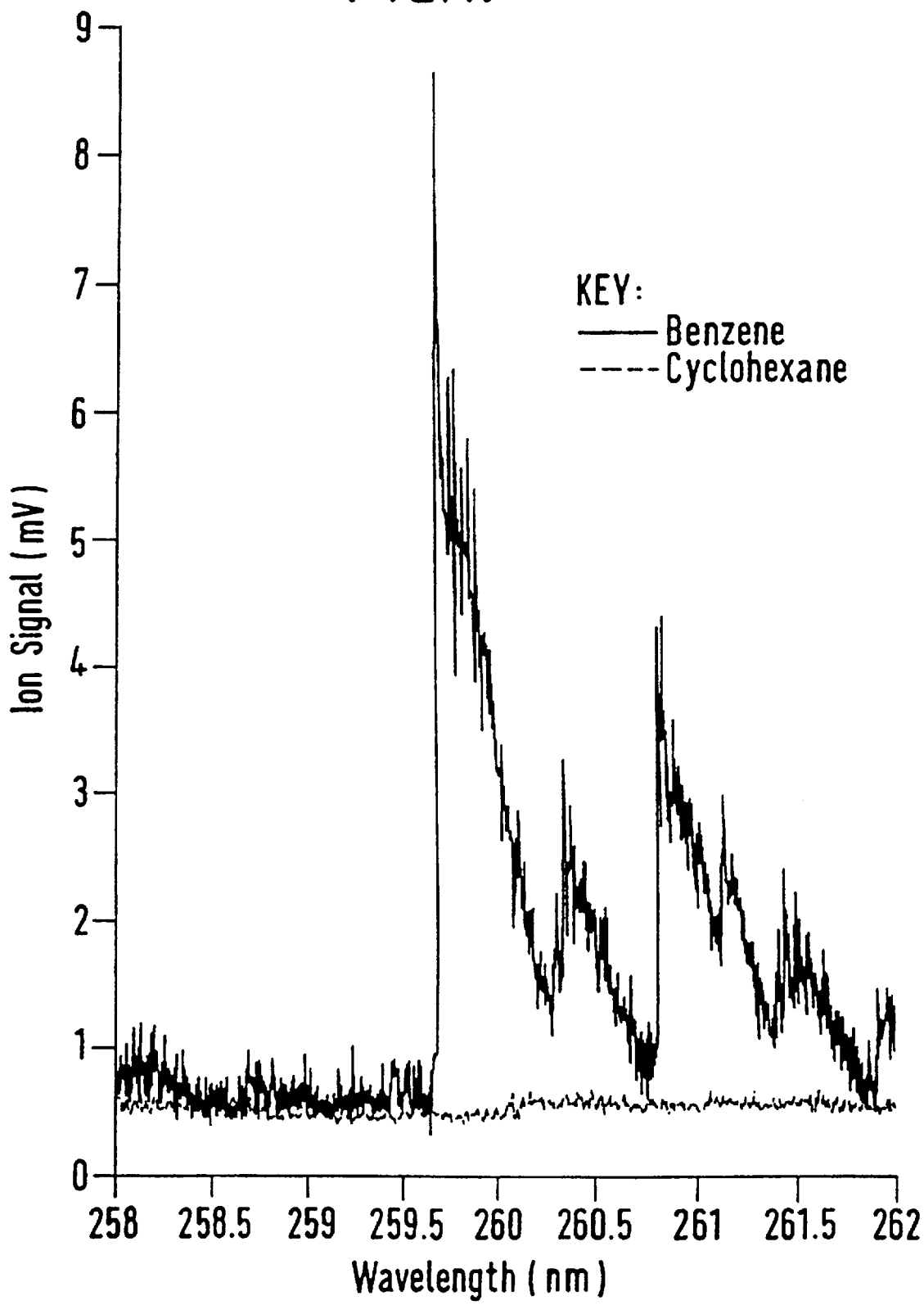
FIG. 19 is a microelectrode REMPI spectra for benzene and cyclohexane.

REMPI spectra of benzene and cyclohexane were also determined at 1 atm and ambient temperature using the microelectrode process. Cyclohexane and benzene in argon carrier gas were photoionized by passage of a pulsed UV laser beam in the 258–262 nm range within 1–2 mm of the probe tip. A DC bias of +500 V from a power source was applied to the anode to collect the photoelectrons. The resulting REMPI spectra are shown in FIG. 19 and are similar to the spectra obtained by the TOF-MS shown in FIG. 18, with expected spectral broadening observed in the ambient temperature and 1 atm. pressure conditions. This shows that use of the 259.7 laser results in the exclusive and efficient production of benzene REMPI ions in the presence of cyclohexane, argon and hydrogen in the reactor system.

Figure 20:
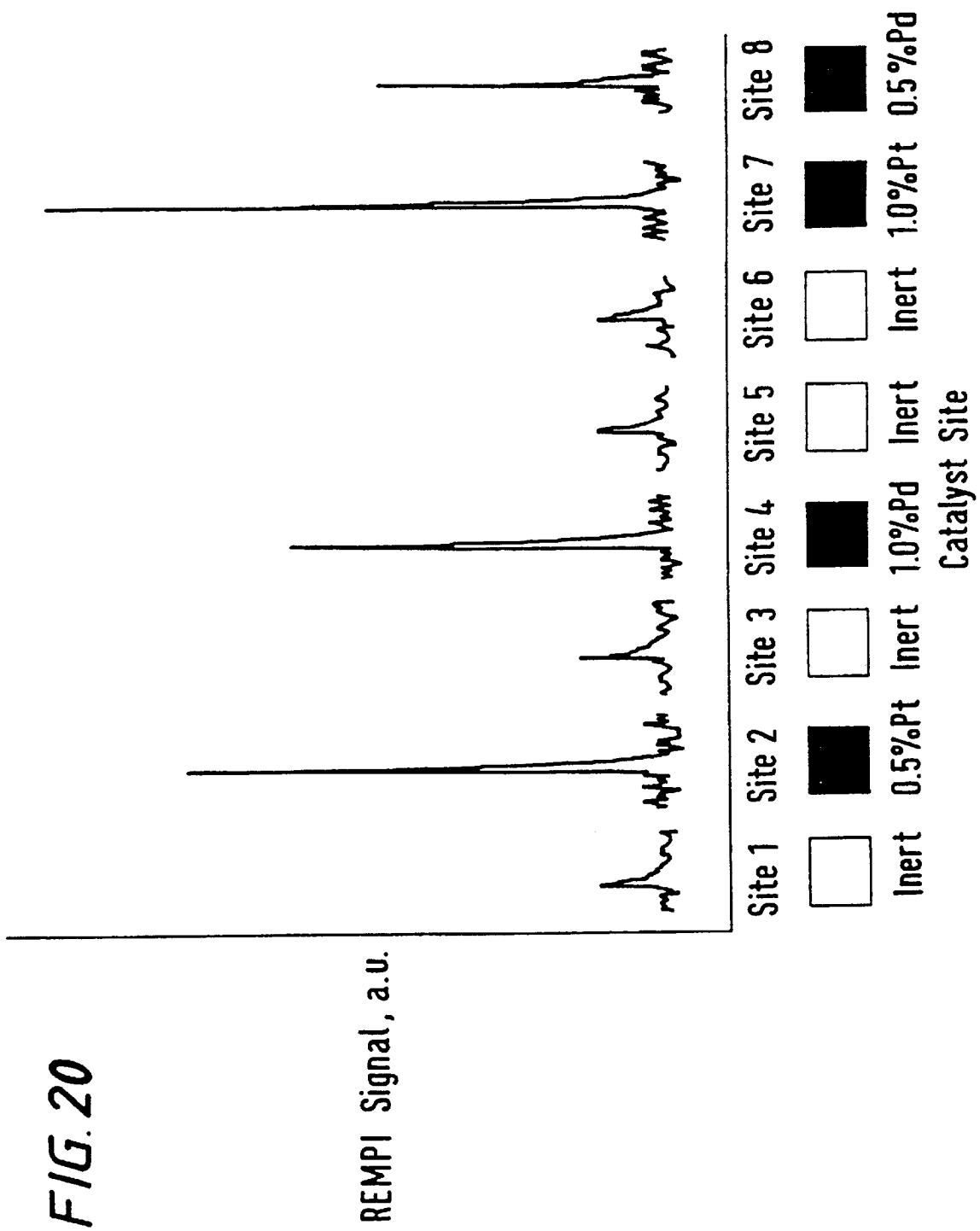
FIG. 20 is microelectrode REMPI signals from screening of catalyst library site activity for benzene production.

The reactor system shown in FIG. 9 was used passing cyclohexane in argon carrier gas through the eight library sites in a row, as identified above. The 259.7 nm laser beam was passed through the product plume from the library sites and the benzene REMPI signals detected in the vicinity of each of the eight sites are shown in FIG. 20. These measurements correspond to data acquired by one laser shot and the signals exhibited fast rise and decay time, in the order of microseconds. As evident from FIG. 20, microelectrodes located at sites 2, 4, 7 and 8 picked up appreciable benzene signals, consistent with the presence of Pt and Pd catalysts at these sites. While some REMPI signals were also detected at sites 1, 3, 5 and 6, they were significantly lower, consistent with the absence of catalysts at these sites. Evidently some benzene was present in the reactor bulk gas due to low gas flow rates and recirculation patterns present in the reactor, both of which reduce the rapid removal of reaction products from the reactor. A smaller reactor chamber, use of monolithic structures or other library designs would reduce this problem. Nevertheless, FIG. 19 shows that the method of this invention rapidly and clearly distinguished between active and inactive sites in the library. The reactor exhaust gases were also analyzed by the TOF-MS using the 259.7 nm laser beam during screening to ascertain whether species other than benzene could have contributed to the measured microelectrode signals. No photoions other than those with mass 78 were detected.

Based upon the magnitude of the REMPI signals measured, as shown in FIG. 20, the relative activities of the catalytic sites appear to be 7>2>4>8. These results are consistent with the relative loadings of the Pd and Pt commercial catalysts at these sites, and also suggest that Pt is a more active cyclohexane dehydrogenation catalyst than Pd. These findings are in agreement with results using conventional catalytic reactor systems. Rehbon, D. M. and Haensel, V., 1988, supra and Ahmed, K. and Chowdhury, H. M., "Dehydration of Cyclohexane and Cyclohexene over Supported Nickel and Platinum Catalysts", Chem. Eng. J., 50, 165, 1992.

It should be recognized that the conditions specified in the above description and example are meant to illustrate the application of the catalyst screening technique of this invention. One skilled in the art can infer from this description and example that the method of this invention can be used to screen any catalyst for any reaction. The reaction conditions can be broadly varied without change in the screening method. For example, the reaction temperature can easily be varied from room temperature, such as 25° C., to higher temperatures, such as 1000° C. Similarly, the pressure can be varied from vacuum, such as $10^{-4}$ Torr, to high pressures, such as 500 atmospheres. The screening process can easily accomodate a wide range of reactant feed concentrations from pure components, 100%, to very dilute streams, such as a few hundred parts per million, 100 ppm.

Combinatorial catalyst libraries can also be generated by machining miniature reactors using integrated circuit manufacturing steps such as thin film deposition, lithography, etching, plasma processing and the like. This approach has been used recently to make a reactor on a chip for the catalytic oxidation of ammonia, as described in Srinivasan, R., Hsing, I. M., Berger, P. E., Jensen, K. F., Firebaugh, S. L., Schmidt, M. A., Harold, M. P., Lerou, J. J. and Ryley, J. F., "Micromachined Reactor for Catalytic Partial Oxidation Reactions", AIChE Journal, 43, 3059–3069, 1997. Unlike monolithic or honeycomb structures which are passive, the micromachined reactors can also incorporate flow and temperature sensors, heating elements and actuators for the control of operating conditions. In this invention, a large number of microreactors are prepared in parallel using any suitable integrated circuit manufacturing sequence. Each microreactor system includes passages for reactant feed, catalytic reaction, product exit, and radiation access. These passages can be machined by either wet or dry etching of an inert wafer substrate, such as silica or alumina, or materials which are coated by such inert films, for example, metals coated by inert materials. The exit passage of each reaction zone should be large enough to accommodate a microelectrode for detection of product REMPI ions. Sensing, flow and temperature controllers can also be embedded into the individual reactor sites on the wafer. In addition, electrical circuitry can be embedded to electrochemically control the catalytic reactions. Different catalytic materials can be deposited into different reactor passages of the library by a variety of techniques, such as, for example, sputtering, laser ablation, thermal or plasma enhanced chemical vapor deposition, and the like, with the use of masks. Alternatively, catalysts can be deposited into the reactor passages using solution techniques with the aid of micro-jet or micro-drop dispensers. These dispensers can also be used to deposit slurries containing catalyst particles. When using solution techniques, the reactor passages can be modified in the reaction zone to contain the necessary amounts of liquid and/or slurry catalyst precursors. This can be accomplished, for example, by machining a reservoir in a central region of the reactor passage for collection of liquid or slurry catalyst precursor mixtures. These reservoirs may be of any shape and can also have internal baffles, actuators and sensors to better control the preparation of catalysts and operation of the reactors during the screening process. The reservoirs can also be placed at different locations along the microreactors to control pressure drop, reactant preheat and product quench conditions. Liquid and/or slurry mixtures of catalyst precursors may be introduced into the reservoirs using micro-jet or micro-drop dispensers and robotics. Following the addition of the liquids, agitation may be induced, for example, by mechanical vibration, micro-activators or sonication, to assure mixing of the liquid or slurry mixtures. After dispensing the catalyst precursors, the resulting mixtures are thermally and chemically treated for the formation of catalysts. These treatment processes may include drying, calcining, oxidation, reduction and activation.

Figure 21:
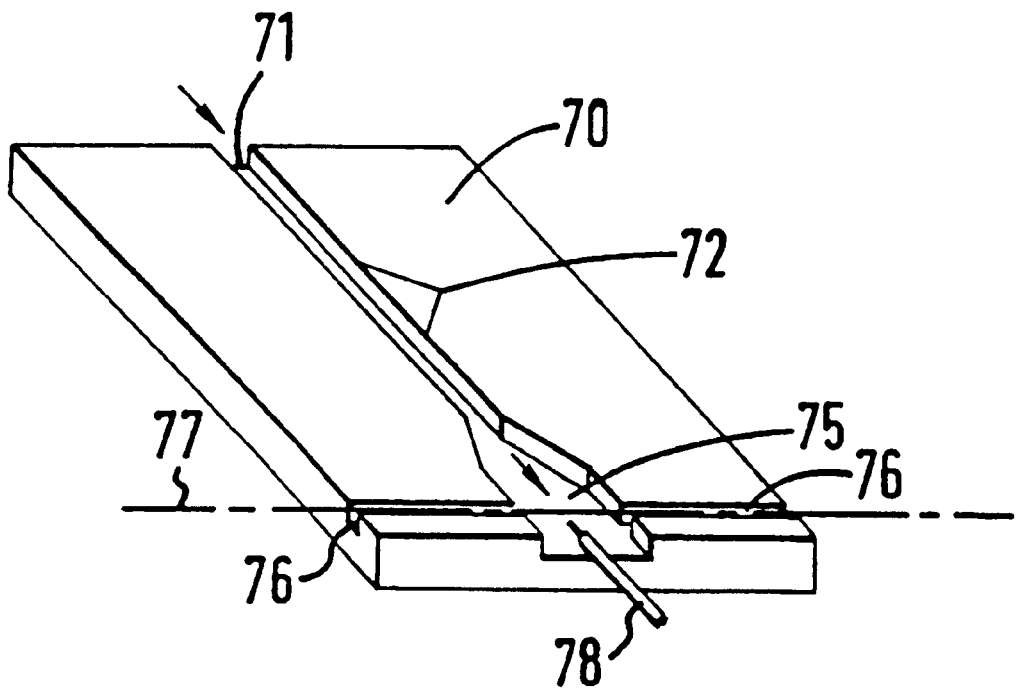
FIG. 21 is a schematic showing of one embodiment of a single microreactor system of this invention.
Figure 22:
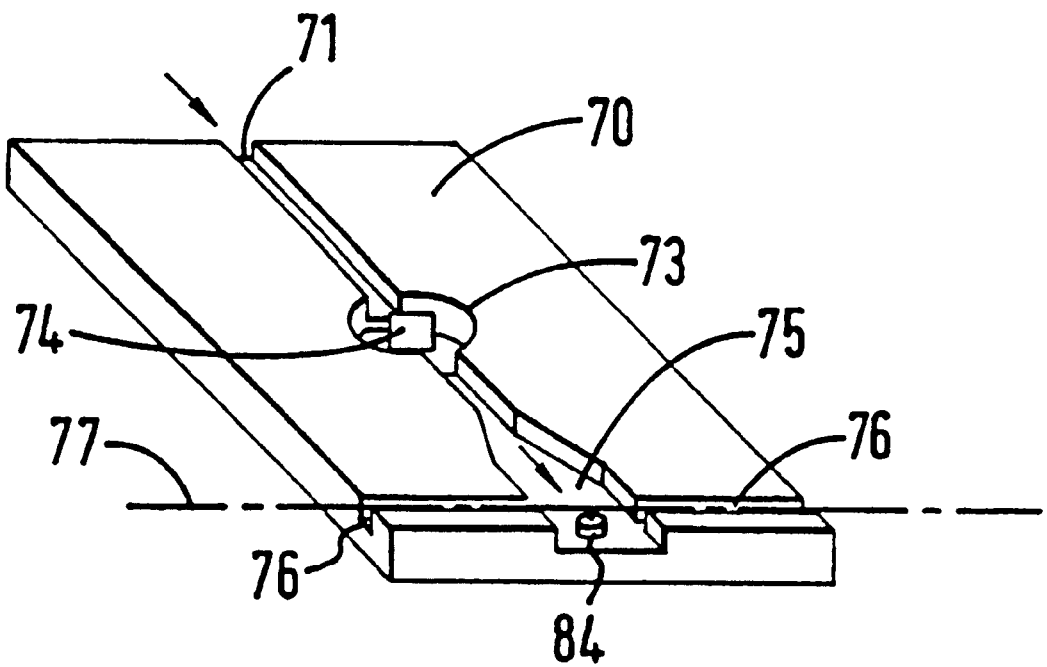
FIG. 22 is a schematic showing of another embodiment of a single microreactor system of this invention suitable for solution deposition.

FIGS. 21 and 22 are simplified schematic showings of bases for single microreactor systems according to this invention. FIG. 21 shows a microreactor suitable for thin film or solid particle catalyst deposition processes and FIG. 22 shows a microreactor additionally suitable for solution based catalyst deposition processes. In the figures, inert microreactor body 70 has reactant feed passage 71 leading to a catalyst zone, shown in FIG. 21 as zone 72 and in FIG. 22 as enlarged reservoir catalyst zone 73. As shown in FIG. 22, baffle structure 74 may be located in reservoir 73. Such baffle structures may have a number of effects, such as, providing additional exposed surface area for the catalyst and for inducing mixing to benefit some reactions. Products exit the reaction volume through exit passage 75. Reactant feed and product flow are shown by the arrows. Activating radiation passages 76, having optical access windows for isolation of exit passage 75, are provided to direct passage of activating radiation beam 77 through the product stream passing through exit passage 75. FIG. 21 shows external microelectrode 78 and FIG. 22 shows internal microelectrode positioned in exit passage 75 in proximity to the activating radiation beam 77 to collect photoelectrons or photoions for detection, as previously described. Internal microelectrode 84 is attached to microreactor body 70, such as embedded to the bottom, side or top walls of the product exit passage, and is thus an integral part of the microreactor body. These internal microelectrodes may be flush with the product exit passage walls or may protrude from them. The internal microelectrodes are provided with suitable wiring for powering the microelectrodes and for passage of detected signals to a detection measurement device. These wirings and connections are embedded in the microreactor body during fabrication using established microelectronics manufacturing techniques.

FIG. 23, wherein the numerals referred to above have the same meaning, schematically shows an array of microreactors in a single inert microreactor body 70. Any number of microreactors may be present in the array, depending upon the size of the microreactors and the physical characteristics of the substrate wafer. Each microreactor 72 can be of any size, however, reactor channels in the order of about 0.1 to 2 millimeters wide are most suitable for fabrication and subsequent screening processes. Reactant plenum 79 is in fluid communication with each reactant feed passageway 72 to distribute reactants to each microreactor. Reactant plenum 79 is sufficiently large to insure the establishment of similar fluid flow rates through each microreactor, provided that the pressure drop characteristics of the microreactors are similar. Alternatively, flow sensors and actuators may be fabricated in each microreactor to independently control fluid flow through each of the microreactors. A different catalyst may be placed in each microreactor using, for example, any of the techniques described. The physical forms of these catalysts can be films, as indicated by numeral 86, or powders, as indicated by numeral 85. Fabrication of a microreactor array from a single base wafer insures good alignment of the activating radiation passages 76 and microelectrodes 84, thereby expediting the screening process. Internal electrodes 84 make possible internal wiring for powering the microelectrodes and for passage of detection signals to a detection measurement device. Alternatively, separate and different electrodes, one for the anode and one for the cathode, can be embedded to different walls of the reactor for powering and signal detection. Suitable connectors may be located on the exterior of the array for easy connection of the entire array to a power source and a detection measurement device through selective switching. Reactant feed and product flows are shown by the arrows.

Following fabrication of the microreactor base layer, an inert cover wafer 80 is bonded to inert microreactor base 70 to cover the microreactor array, as shown in FIG. 24, to isolate each microreactor system while allowing the flow of reactant in and the flow of products out of the microreactor array. FIG. 24 shows internal microelectrodes 87 attached to or embedded in cover wafer 80 in similar manner as described with respect to internal microelectrodes 84 attached to microreactor body 70, as disclosed above. Internal wiring 88 leads from each microelectrode 87 to external connector 89 for powering each microelectrode and for passage of detection signals from each microelectrode to a detection device. Alternatively, separate electrodes can be embedded to the base 70 for signal detection and/or for power supply. Heating elements may be embedded in thermal conducting microreactor body 70 between microreactor chambers 72 and/or in thermal conducting cover wafer 80 and/or in thermal conducting sheets between stacked reactor arrays to provide desired temperature control to the microreactors and/or reactant feed channels. As shown in FIG. 25, individual flat microreactor arrays, as shown in FIG. 24, may be stacked vertically to obtain three dimensional structures of a plurality of flat microreactor arrays, thereby providing rapid analysis of a large number of samples in the manner similar to that shown in FIG. 12. The microreactor arrays may have any suitable fasteners for maintaining adjacent arrays in fixed relationship with each other. The microelectrodes are powered by DC power source and the signal from each microelectrode fed through a multi-channel selector to measurement device.

Figure 26:
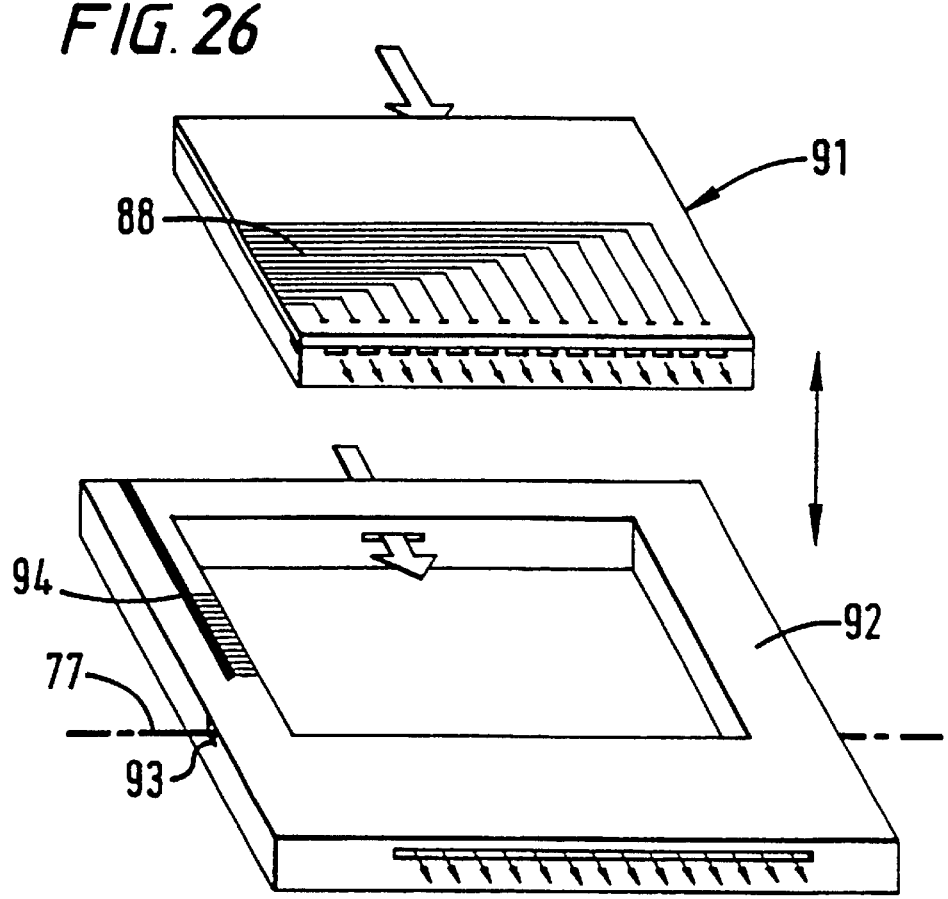
FIG. 26 is a schematic showing a microreactor array as shown in FIG. 24 fitting into a frame.

FIG. 26 shows a microreactor array 91, as shown in FIG. 24, may be placed in microreactor array frame 92 for easy handling and connection for catalyst screening. The microreactor array fits into an opening in the frame as indicated by the reversible arrow. Reactant feed is provided through the frame to the reactant feed manifold of the microreactor array, as indicated by the arrows, and product exits through the frame, as indicated by the arrows. Radiation passages 93 are provided through frame 92 for entry and exit of radiation beam 77 aligned to pass through radiation passages 76 in microreactor body 70, as described above. The frame also has internal wiring 94 for connection at one end to internal wiring 88 of the microreactor array and at the opposite end to a power source and a detection measurement device. The internal wiring of a plurality of microreactor array frames may connect through a single connector to external wiring. The frames may also have reactant feed manifolds arranged so that a single feed supply can provide reactant to a plurality of microreactor array—frame assemblies. The frames may also provide temperature control for the microreactor array through heating elements built into the frames. Microreactor array—frames may have any suitable means for connection of adjacent microreactor array frame assemblies.

Figure 27:
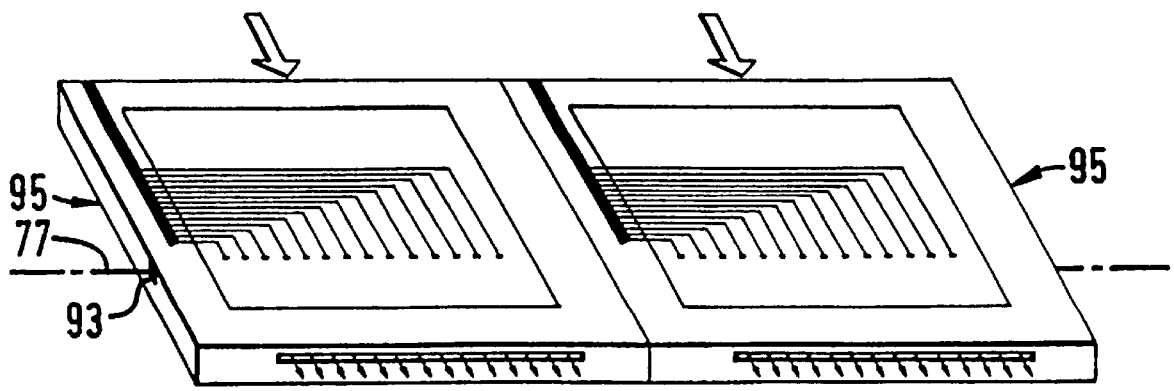
FIG. 27 is a schematic showing of arrays of microreactors in frames as shown in FIG. 26 arranged in adjacent side-by-side configuration.

A plurality of microreactor—frame assemblies may be joined in a vertical fashion similar to that shown in FIG. 25. In another embodiment, shown in FIG. 27, microreactor array—frame assemblies 95 may be joined horizontally in side-by-side relation. Alignment of radiation passages 93 makes it possible to use one radiation beam 77 in the evaluation of large catalyst libraries.

Screening is accomplished by passing a known amount of reactant gases through the microreactor array in contact with the potential catalysts forming reaction products which are activated by passing a suitable tunable radiation beam through activating radiation passages 76, having access windows providing fluid isolation, to form product REMPI ions in the product exit passages 75. These product REMPI ions are detected by the microelectrodes within the exit passages and measured in manners described above. During screening, the microreactor arrays may be placed in a furnace for temperature control of the entire array or the temperature of each microreactor may be independently controlled using sensors and heating elements built into the microreactors during the microreactor fabrication process. Alternatively, temperature control can be provided by the frame.

FIGS. 28A and 28B summarize another example of combinatorial catalyst library preparation and screening method using a different microreactor array and microdrop/microjet technology according to this invention. Step 1 shows preparation of the catalyst library inert substrate using a plug to form desired passageways and to retain liquid during solution deposition. Step 2 shows catalyst precursor solution deposition into reservoirs of catalyst reaction zones. Step 3 shows drying and calcining of the catalyst by methods well known in the art. Step 4 shows opening of the product exit passages by removal of the plugs used to form the passages. Step 5 shows formation and/or activation of the catalyst by passage of a suitable gas through the microreactor array. Step 6 shows screening of the catalysts within the array of microreactors by passing reactant gas(s) in contact with the catalyst in each microreactor, passing a radiation beam of an energy level to promote formation of specified ions through each reaction product stream, and detecting the formed ions or electrons by microelectrode collection in proximity to the activating radiation beam.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

I claim:

1. A microreactor and sampling probe system for mass spectrometric and microelectrode screening of catalytic and potential catalytic reaction products, said system comprising; a plurality of addressable microreactors, each microreactor comprising, an inert substrate body, a reactor passageway extending from a first opening on one side of said substrate body to a second opening on an opposite side of said substrate body, a reaction zone in a central portion of said reactor passageway serving as a reaction zone for contact of reactants with a catalyst in said reaction zone, a reactant zone of said reactor passageway extending from said reaction zone to said first opening and serving as a reactant feed passage, and a product zone of said reactor passageway extending from said reaction zone to said second opening and serving as a product exit passage; a tubular sampling probe comprising at one end a sampling orifice forming a free jet expansion stream into a substantially expanded chamber of at least one vacuum stage and an open opposite end connectable to an inlet orifice of a mass spectrometer; a radiation beam passageway extending through said substrate body generally perpendicular to and intersecting said product zone, said radiation beam passageway having radiation beam access windows providing passage of a radiation beam and fluid isolation of said radiation beam passageway from said product zone; a microelectrode in said product zone in proximity to the intersection of said radiation beam passageway with said product zone; and a translation mechanism capable of placing said sampling orifice of said tubular sampling probe in proximity to said product exit passage of a first addressable single microreactor for a sampling mode and rapidly translating to position said sampling orifice in a position in proximity to the product exit passage of a second addressable single microreactor for a sampling mode of said second microreactor.

2. A system according to claim 1 wherein said sampling orifice is about 1 to about 200 micrometers in diameter located at the vertex of an expansion cone having a half cone angle of about 15 to about 45 degrees.

3. A system according to claim 1 wherein said sampling orifice is a short capillary having a diameter of about 1 to about 500 micrometers and a length of about 1 micrometer to about 200 micrometers.

4. A system according to claim 3 wherein said capillary has a diameter of about 5 to about 20 micrometers.

5. A system according to any one of claims 1 to 4 wherein the distance from said sampling orifice to said inlet orifice of said mass spectrometer is about 3 to about 10 inches.

6. A system according to any one of claims 1 to 4 wherein said expanded chamber comprises two vacuum stages having a skimming orifice between a first and second vacuum stage.

7. A system according to any one of claims 1 to 4 wherein said plurality of microreactors is an in-line array of microreactors fixidly mounted on a translation table rapidly movable along an x axis for alignment of said sampling orifice and said product exit passage and along a z axis for placement of said sampling orifice and said product exit passage in proximity to each other.

8. A system according to any one of claims 1 to 4 wherein said plurality of microreactors is a parallel stack of a plurality of in-line arrays of microreactors fixidly mounted on a translation table rapidly movable along x and y axes for alignment of said sampling orifice and said product exit passage and along a z axis for placement of said sampling orifice and said product exit passage in proximity to each other.

9. A system according to any one of claims 1 to 4 wherein each said microreactor comprises temperature and flow controls for individual control of temperature and flow in each microreactor.

10. A system according to any one of claims 1 to 4 wherein each said microreactor comprises an insert for placement in and removal from said reaction zone for catalyst loading.

11. A process for rapid screening of potential catalyst libraries for catalytic properties, comprising; forming a potential catalyst library having potential catalysts at a plurality of addressable test sites; passing reactant gas in contact with said potential catalysts in at least one of said plurality of addressable sites; and screening gas plumes of reaction products from said addressable sites, said screening comprising translating at least one of a sampling probe and said library to a position that one addressable site is in proximity to a sampling probe orifice, passing a portion of said reaction products from said one addressable site through said sampling probe orifice forming a free jet expansion stream in a substantially expanded volume of at least one vacuum stage thereby cooling and reducing the pressure of the jet stream of said reaction products to a pressure suitable for introduction into a mass spectrometer, and passing a portion of the jet stream of reaction products at reduced pressure through an inlet orifice into a mass spectrometer for analysis, said screening additionally comprising passing at least one radiation beam of an energy level to promote formation of energized products comprising specified ions and electrons through said gas plume of reaction products from said one addressable site and detecting in real time said formed ions or electrons by microelectrode collection in situ in proximity to said one addressable site.

12. A process according to claim 11 wherein said sampling probe orifice is about 1 to about 200 micrometers in diameter located at the vertex of an expansion cone having a half cone angle of about 15 to about 45 degrees.

13. A process according to claim 11 wherein said sampling probe orifice is a short capillary having a diameter of about 1 to about 500 micrometers and a length of about 1 micrometer to about 200 micrometers.

14. A process according to claim 13 wherein said capillary has a diameter of about 5 to about 20 micrometers.

15. A process according to any one of claims 11 to 14 wherein the distance from said sampling probe orifice to said inlet orifice of said mass spectrometer is about 7.5 to about 25 centimeters.

16. A process according to any one of claims 11 to 14 wherein said expanded chamber comprises two vacuum stages having a skimming orifice between a first and second vacuum stage.

17. A process according to any one of claims 11 to 14 further comprising contacting said reaction products with at least one energy beam forming fragmentation daughter product(s), said screening and said detecting being performed on said fragmentation daughter product(s).

18. A process according to any one of claims 11 to 14 wherein said plurality of addressable test sites comprise microreactors in a parallel stack of a plurality of in-line arrays of microreactors fixidly mounted on a translation table rapidly movable along x and y axes for alignment of said sampling probe orifice and a reaction product exit passage from a single addressable microreactor and along a z axis for placement of said sampling orifice and said product exit passage in proximity to each other.

* * * * *